US007176279B2

(12) United States Patent
Sharma et al.

(10) Patent No.: US 7,176,279 B2
(45) Date of Patent: *Feb. 13, 2007

(54) CYCLIC PEPTIDE COMPOSITIONS AND METHODS FOR TREATMENT OF SEXUAL DYSFUNCTION

(75) Inventors: Shubh Sharma, Cranbury, NJ (US); Annette Shadiack, Somerset, NJ (US); Ramesh Rajpurohit, Hillsboro, NJ (US); Wei Yang, Edison, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 156 days.

This patent is subject to a terminal disclaimer.

(21) Appl. No.: 10/638,071

(22) Filed: Aug. 8, 2003

(65) Prior Publication Data

US 2004/0138136 A1  Jul. 15, 2004

Related U.S. Application Data

(63) Continuation-in-part of application No. 10/040,547, filed on Jan. 4, 2002, now Pat. No. 6,794,489, which is a continuation-in-part of application No. 09/606,501, filed on Jun. 28, 2000, now Pat. No. 6,579,968.

(51) Int. Cl.
*A61K 38/00* (2006.01)
*A61K 38/12* (2006.01)
*C07K 7/00* (2006.01)

(52) U.S. Cl. ............... 530/312; 530/317; 530/321; 530/300; 530/328; 530/329; 514/9; 514/11; 514/12; 514/15; 514/16; 514/18; 424/9.1; 436/811

(58) Field of Classification Search ............... 530/312, 530/317, 321, 300, 328, 329; 514/9, 11, 514/12, 15, 16, 18; 424/9.1; 436/811
See application file for complete search history.

(56) References Cited

U.S. PATENT DOCUMENTS

| 3,853,836 | A | | 12/1974 | Greven |
| 3,862,928 | A | | 1/1975 | De Wied et al. |
| 4,649,191 | A | * | 3/1987 | Hruby .................. 530/329 |
| 4,696,913 | A | | 9/1987 | Geiger et al. |
| 5,420,109 | A | | 5/1995 | Suto et al. |
| 5,569,647 | A | * | 10/1996 | Fauchere et al. ............ 514/11 |
| 5,576,290 | A | | 11/1996 | Hadley |
| 5,674,839 | A | | 10/1997 | Hruby et al. |
| 5,693,608 | A | | 12/1997 | Bechgaard et al. |
| 5,714,576 | A | | 2/1998 | Hruby et al. |
| 5,731,408 | A | | 3/1998 | Hadley et al. |
| 5,908,825 | A | | 6/1999 | Fasano et al. |
| 5,977,070 | A | | 11/1999 | Piazza et al. |
| 6,051,555 | A | | 4/2000 | Hadley |
| 6,054,556 | A | | 4/2000 | Huby et al. |
| 6,579,968 | B1 | * | 6/2003 | Blood et al. .................. 530/312 |

| 6,794,489 | B2 | * | 9/2004 | Blood et al. .................. 530/312 |

FOREIGN PATENT DOCUMENTS

| FR | 2 691 465 | 11/1993 |
| FR | 2 735 131 | 12/1996 |
| WO | WO94/22460 | 10/1994 |
| WO | WO99/21571 | 5/1999 |
| WO | WO99/43709 | 9/1999 |
| WO | WO99/55679 | 11/1999 |
| WO | WO99/64002 | 12/1999 |
| WO | WO03/006620 A2 | 1/2003 |

OTHER PUBLICATIONS

Miklós Löw, et al., "Role of Chain Termini in Selective Steroidogenic Effect of ACTH/MSH(4-10) on Isolated Adrenocortical Cells", *Peptides*, 1990, pp. 29-31, vol. 11.
Maria A. Bednarek, et al., "Structure-function studies on the cyclic peptide MT-II, lactam derivative of a-melanotropin", *Peptides*, 1999, pp. 401-409, vol. 20.
Mac E. Hadley, et al., "Melanocortin Receptors: Identification and Characterization by Melanotropic Peptide Agonists and Antagonists", *Pigment Cell Research*, Sep. 1996, pp. 213-234.
Carrie Haskell-Luevano, et al., "Discovery of Prototype Peptidomimetic Agonists at the Human Melanocortin Receptors MC1R and MC4R", *Journal of Medicinal Chemistry*, 1997, pp. 2133-2138, vol. 40, No. 14.
Victor J. Hruby, et al., "Cyclic Lactam a-Melanotropin Analogues of Ac-Nle$^4$-cyclo[Asp$^5$, D-Phe$^7$, Lys$^{10}$] a-Melanocyte-Stimulating Hormone-(4-10)-NH$_2$ with Bulky Aromatic Amino Acids at Position 7 Show High Antagonist Potency and Selectivity at Specific Melanocortin Receptors", *Journal of Medicinal Chemistry*, 1995, pp. 3454-3461, vol. 38.
Helgi B. Schiöth, et al., "Discovery of novel melanocortin$_4$ receptor selective MSH analogues", *British Journal of Pharmacology*, 1998, pp. 75-82, vol. 124.
Helgi B. Schiöth, et al., "Selective properties of C- and N-terminals and core residues of the melanocyte-stimulating hormone on binding to the human melanocortin receptor subtypes", *European Journal of Pharmacology*, 1998, pp. 359-366, vol. 349.
Hunter Wessells, et al., "Synthetic Malanotropic Peptide Initiates Erections in Men with Psychogenic Erectile Dysfunction; Double-Blind, Placebo Controlled Crossover Study", *The Journal of Urology*, Aug. 1998, pp. 389-393, vol. 160.
John Donlon. et al., "The Production of Biological Active Peptides in Brain Tissues", *Metabolism of Brain Peptides*, 1995, CRC Press, Inc., Boca Raton, Florida.
Gerard O'Cuinn, et al., "Neuropeptide Inactivation by Peptidases", *Metabolism of Brain Peptides*, 1995, CRC Press, Inc., Boca Raton, Florida.

* cited by examiner

*Primary Examiner*—Chih-Min Kam
(74) *Attorney, Agent, or Firm*—Stephen A. Slusher

(57) ABSTRACT

A cyclic peptide with a C-terminus —OH group. Further provided are compositions and methods for treatment of sexual dysfunction in mammals, including male sexual dysfunction, such as erectile dysfunction, and female sexual dysfunction, by administration of a cyclic peptide including a C-terminus —OH group. Methods of administration include injection, oral, urethral, vaginal, nasal and mucosal administration.

19 Claims, No Drawings

CYCLIC PEPTIDE COMPOSITIONS AND METHODS FOR TREATMENT OF SEXUAL DYSFUNCTION

CROSS-REFERENCE TO RELATED APPLICATIONS

This application is a continuation-in-part application of U.S. patent application Ser. No. 10/040,547, entitled Compositions and Methods for Treatment of Sexual Dysfunction, filed on Jan. 4, 2002, now U.S. Pat. No. 6,794,489, which is a continuation-in-part application of U.S. patent application Ser. No. 09/606,501, now U.S. Pat. No. 6,579,968, entitled Composition and Methods for Treatment of Sexual Dysfunction, which application was filed on Jun. 28, 2000 and issued as a patent on Jun. 17, 2003, and the benefit of the filing of each pursuant to 35 U.S.C. § 120 and specification thereof of each is incorporated herein by reference.

This application claims the benefit of the filing of International Application No. PCT/US02/22196, International Publication No. WO 03/006620, entitled *Linear and Cyclic Melanocortin Receptor-Specific Peptides*, filed on Jul. 11, 2002; U.S. Provisional Patent Application Ser. No. 60/304,836, entitled *Linear and Cyclic Melanocortin Receptor-Specific Peptides*, filed on Jul. 11, 2001; U.S. Provisional Patent Application Ser. No. 60/142,346, entitled *Compositions And Methods For Treatment Of Sexual Dysfunction*, filed on Jun. 29, 1999, and U.S. Provisional Patent Application Ser. No. 60/194,987, entitled *Compositions And Nasal Delivery Methods For Treatment Of Sexual Dysfunction*, filed on Apr. 5, 2000, and the benefit of the filing of each pursuant to 35 U.S.C. § 119 or § 120 and specification thereof of each is incorporated herein by reference.

BACKGROUND OF THE INVENTION

1. Field of the Invention (Technical Field)

The present invention relates to cyclic peptides with a C-terminus free acid, use thereof in pharmaceutical compositions for the treatment of sexual dysfunction in animals, including both male erectile dysfunction and female sexual dysfunction, and methods for the use and administration of such cyclic peptides and pharmaceutical compositions.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Sexual dysfunction, including both penile erectile dysfunction or impotence and female sexual dysfunction, is a common medical problem. Significant effort has been devoted over the last twenty or more years to develop methods, devices and compounds for treatment of sexual dysfunction. While more effort has been undertaken for treatment of penile erectile dysfunction, female sexual dysfunction is also an area to which significant research and effort has been devoted.

At present, one commonly used orally administered drug for treatment of sexual dysfunction in the male is Viagra®, a brand of sildenafil, which is a phosphodiesterase 5 (PDE-5) inhibitor, increasing the persistence of cyclic guanosine monophosphate and thereby enhancing erectile response. Another drug approved in Europe for treating male erectile dysfunction is Ixense®, a brand of apomorphin that is a non-selective dopa receptor agonist. Oral and nasal formulations of apomorphin are currently undergoing clinical evaluations in the United States. There are several other medical treatment alternatives currently available depending on the nature and cause of the impotence problem. Some men have abnormally low levels of the male hormone testosterone, and treatment with testosterone injections or pills may be beneficial. However, comparatively few impotent men have low testosterone levels. For many forms of erectile dysfunction, treatment may be undertaken with drugs injected directly into the penis, including drugs such as papaverin, prostaglandin E1, phenoxybenzamine or phentolamine. These all work primarily by dilating the arterial blood vessels and decreasing the venous drainage. Urethral inserts, such as with suppositories containing prostaglandin, may also be employed. In addition, a variety of mechanical aids are employed, including constriction devices and penile implants.

A number of other agents have been shown to induce or facilitate penile erection in laboratory animals. These include very diverse classes of ligands such as oxytocin (Benelli A, Poggioli R, Luppi P, Ruini L, Bertolini A, Arletti R, Oxytocin enhances, and oxytocin antagonism decreases, sexual receptivity in intact female rats. *Neuropeptides* 27:245–50 (1994)), vasopressin, vasoactive intestinal peptide, melanotropins, and ACTH as well as their analogs.

A variety of treatments have also been explored for female sexual dysfunction, including use of sildenafil, although the Food and Drug Administration has not specifically approved such use. Testosterone propionate has also been employed to increase or augment female libido.

Melanocortin receptor-specific compounds have been explored for use of treatment of sexual dysfunction. In one report, a cyclic α-melanocyte-stimulating hormone ("α-MSH") analog, called Melanotan-II, was evaluated for erectogenic properties for treatment of men with psychogenic erectile dysfunction. Wessells H. et al., *J Urology* 160: 389–393 (1998); see also U.S. Pat. No. 5,576,290, issued Nov. 19, 1996 to M. E. Hadley, entitled *Compositions and Methods for the Diagnosis and Treatment of Psychogenic Erectile Dysfunction* and U.S. Pat. No. 6,051,555, issued Apr. 18, 2000, also to M. E. Hadley, entitled *Stimulating Sexual Response in Females*. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled *Cyclic Analogs of Alpha-MSH Fragments*, and in U.S. Pat. No. 5,714,576, issued Feb. 3, 1998, to V. J. Hruby, M. E. Hadley and F. Al-Obeidi, entitled *Linear Analogs of Alpha-MSH Fragments*. Additional related peptides are disclosed in U.S. Pat. Nos. 5,576,290, 5,674,839, 5,714,576 and 6,051,555. These peptides are described as being useful for both the diagnosis and treatment of psychogenic sexual dysfunction in males and females. These peptides are related to the structure of melanocortins. Other peptides are disclosed in U.S. Pat. No. 6,284,735 and U.S. Published Patent Applications Nos. 2001/0056179 and 2002/0004512.

In use of Melanotan-II, significant erectile responses were observed, with 8 of 10 treated men developing clinically apparent erections, and with a mean duration of tip rigidity greater than 80% for 38 minutes with Melanotan-II compared to 3.0 minutes with a placebo (p=0.0045). The drug was administered by subcutaneous abdominal wall injection, at doses ranging from 0.025 to 0.157 mg/kg body weight. Transient side effects were observed, including nausea, stretching and yawning, and decreased appetite.

It has long been believed that erectile response to melanocortin receptor-specific compounds, and both male and female sexual response in general, was related to the central tetrapeptide sequence, His[6]-Phe[7]-Arg[8]-Trp[9] (SEQ ID NO:1) of native α-MSH. In general, all melanocortin peptides share the same active core sequence, His-Phe-Arg-Trp (SEQ ID NO:1), including melanotropin neuropeptides and adrenocorticotropin. MC3-R (the melanocortin-3 receptor) has the highest expression in the arcuate nucleus of the hypothalamus, while MC4-R (the melanocortin-4 receptor) is more widely expressed in the thalamus, hypothalamus and hippocampus. A central nervous system mechanism for melanocortins in the induction of penile erection has been suggested by experiments demonstrating penile erection resulting from central intracerebroventricular administration of melanocortins in rats. While the mechanism of His-Phe-Arg-Trp (SEQ ID NO:1) induction of erectile response has never been fully elucidated, it has been generally accepted that it involves the central nervous system, and binding to MC3-R and/or MC4-R, and according to most researchers, MC4-R.

Non-peptides have been proposed which alter or regulate the activity of one or more melanocortin receptors. For example, International Patent Application No. PCT/US99/09216, entitled *Isoquinoline Compound Melanocortin Receptor Ligands and Methods of Using Same*, discloses two compounds that induce penile erections in rats. However, these compounds were administered by injection at doses of 1.8 mg/kg and 3.6 mg/kg, respectively, and at least one compound resulted in observable side effects, including yawning and stretching. Other melanocortin receptor-specific compounds with claimed application for treatment of sexual dysfunction are disclosed in International Patent Application No. PCT/US99/13252, entitled *Spiropiperidine Derivatives as Melanocortin Receptor Agonists*. International Patent Application Nos. PCT/US00/14930, PCT/US00/19408, WO 01/05401, WO/00/53148, WO 01/00224, WO 00/74679, WO 01/10842 and the like disclose other compounds that may be so utilized.

Both cyclic and linear α-MSH peptides have been studied for sexual dysfunction; however, the peptides heretofore evaluated have had an amide or —NH$_2$ group at the C-terminus. See, for example, Wessells H. et al., *J Urology*, cited above; Haskell-Luevano C. et al., *J Med Chem* 40:2133–39 (1997); Schioth H. B. et al., *Brit J Pharmacol* 124:75–82 (1998); Schioth H. B. et al., *Eur J Pharmacol* 349:359–66 (1998); Hadley M. E. et al., *Pigment Cell Res* 9:213–34 (1996); Bednarek M. A. et al., *Peptides* 20:401–09 (1999); U.S. Pat. Nos. 6,054,556, 6,051,555 and 5,576,290; and, International Patent Applications PCT/US99/04111 and PCT/US98/03298. While significant research has been conducted in an effort to determine the optimal structure of α-MSH peptides, including a variety of structure-function, agonist-antagonist, molecular modeling and pharmacophore studies, such studies have relied upon peptides with an art conventional —NH$_2$ group at the C-terminus. Further, it has long been believed that biologically active neuropeptides, including α-MSH peptides, are amidated, with an —NH$_2$ group at the C-terminus, and that such amidation is required both for biological activity and stability. See, for example, *Metabolism of Brain Peptides*, Ed. G. O'Cuinn, CRC Press, New York, 1995, pp. 1–9 and 99–101.

There remains a need for clinically effective melanocortin receptor-specific agents for use in treatment of sexual dysfunction, including particularly compounds that are effective at low doses, optionally may be administered by minimally invasive means such as oral or nasal administration, which have rapid onset of pharmacological action, and are without significant undesirable side effects.

SUMMARY OF THE INVENTION
(DISCLOSURE OF THE INVENTION)

In one embodiment the invention provides a cyclic peptide of structural formula I:

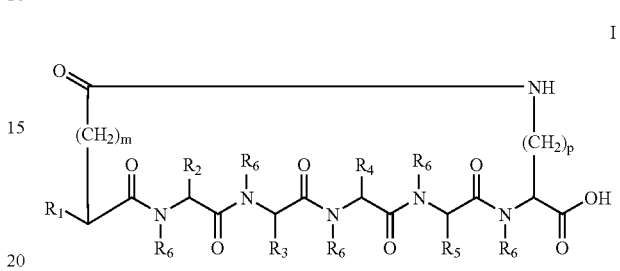

or a pharmaceutically acceptable salt thereof.

In peptides of formula I, $R_1$ is H or

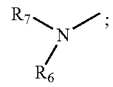

$R_7$ is H, an aliphatic L- or D-amino acid, an N-acylated L- or D-amino acid or a linear or branched $C_1$ to $C_{17}$ alkyl, aryl, heteroaryl, alkene, alkenyl, or aralkyl chain. $R_7$ may thus include a $C_1$ to $C_{17}$ aliphatic linear or branched chain, an omega amino derivative of a $C_1$ to $C_{17}$ aliphatic linear or branched chain, or an acylated derivative of an omega amino derivative of a $C_1$ to $C_{17}$ aliphatic linear or branched chain.

$R_2$, $R_3$ and $R_5$ are independently H, a $C_1$ to $C_6$ aliphatic linear or branched chain, including $CH_3$, or an aromatic amino acid side chain moiety, on the proviso that at least one of $R_3$ and $R_5$ is not H or a $C_1$ to $C_6$ aliphatic linear or branched chain. In a preferred embodiment, both $R_3$ and $R_5$ are aromatic amino acid side chain moieties. Optionally the aromatic amino acid side chain moiety is derived from a natural or synthetic L- or D-amino acid, and is an aromatic substituted aryl or heteroaryl side chain. The aromatic ring or rings of the amino acid side chain moiety may be functionalized with one or more halogens or one or more alkyl or aryl groups. The aromatic amino acid side chain moiety is preferably selected from the following:

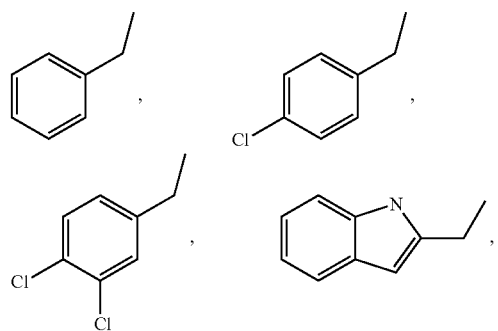

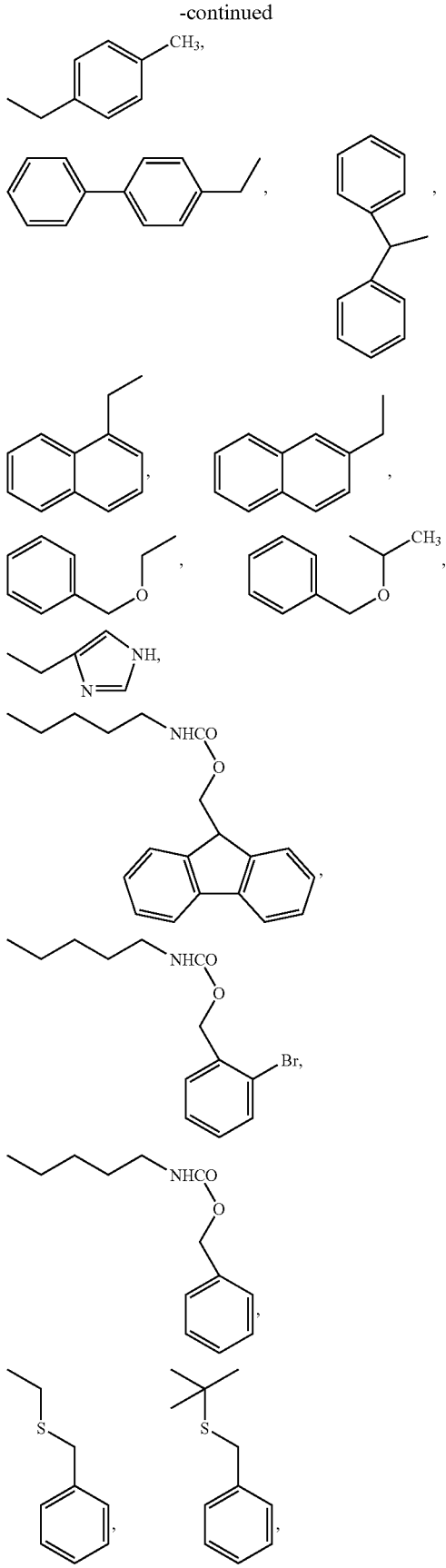

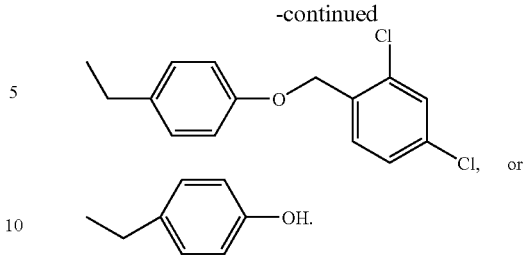

$R_4$ is a $C_1$ to $C_6$ linear or branched chain amino acid side chain or a neutral hydrogen bonding or positively charged amino acid side chain moiety. Optionally the $C_1$ to $C_6$ linear or branched chain is $CH_3$. Optionally the neutral hydrogen bonding or positively charged amino acid side chain moiety is an aliphatic or aromatic amino acid side chain moiety derived from a natural or synthetic L- or D-amino acid, wherein the moiety includes at least one nitrogen-containing group, including an amide, imide, amine, guanidine, urea, urethane, or nitrile. The $R_4$ nitrogen-containing amino acid side chain moiety is preferably selected from the following:

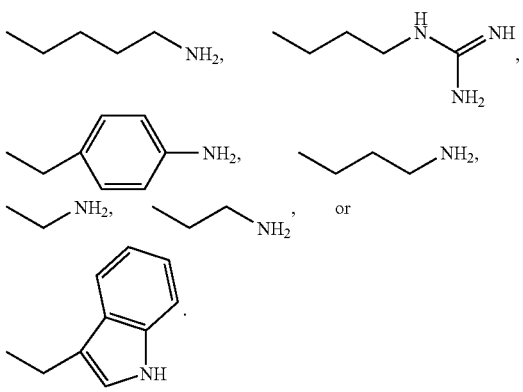

The $R_4$ neutral aliphatic amino acid side chain moiety, wherein the side chain includes hydrogen donors and/or acceptors, is preferably selected from the following:

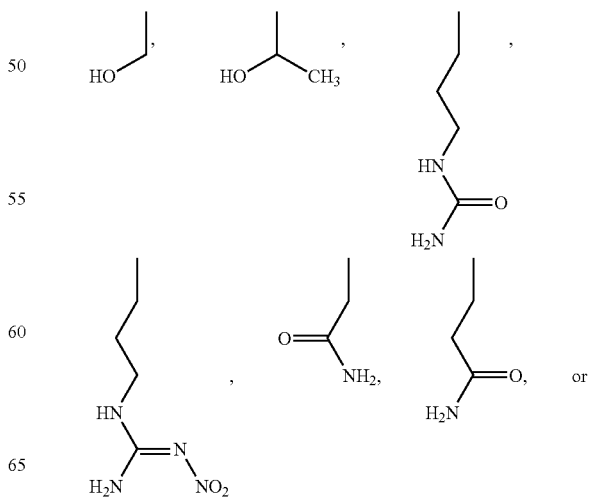

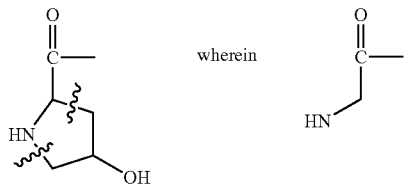

wherein

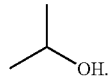

is a portion of the backbone, and $R_5$ is

Each $R_6$ is independently H, a lower aliphatic $C_1$–$C_4$ branched or linear alkyl chain, including methyl or ethyl, a $C_1$–$C_4$ aralkyl, or a $C_1$–$C_4$ omega amino derivative. In a preferred embodiment, each $R_6$ is H; in another preferred embodiment, at least one $R_6$ is not H.

In the peptides of formula I, m is 1 to 4, and p is 1 to 5, provided that m+p is 2 to 7. In a preferred embodiment, m is 1 and p is 4.

In another embodiment, the invention provides a cyclic peptide of structural formula II:

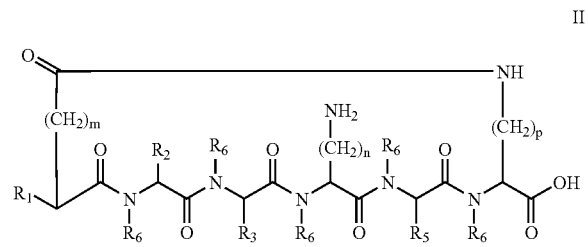

or a pharmaceutically acceptable salt thereof.

In cyclic peptides of structural formula II, $R_1$, $R_2$, $R_3$, $R_5$, $R_6$, $R_7$, m and p are as defined for structural formula I, and n is 1 to 6. The cyclic peptide Ac-Nle-cyclo(-Asp-His-D-Phe-Lys-Trp-Lys)-OH is a representative example of a peptide of structural formula II.

In another embodiment, the invention provides a cyclic peptide of structural formula III:

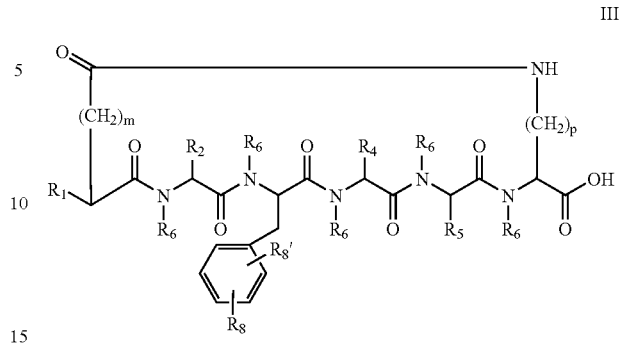

or a pharmaceutically acceptable salt thereof.

In cyclic peptides of structural formula III, $R_1$, $R_2$, $R_4$, $R_5$, $R_6$, $R_7$, m and p are as defined for structural formula I, and each of $R_8$ and $R_8'$ is independently H or a halogen, alkyl or aryl group, on the proviso that at least one of $R_8$ and $R_8'$ is not H. Halogen includes the atoms fluorine, chlorine, bromine and iodine, and groups including one or more halogen atoms, such as —$CF_3$. The cyclic peptide Ac-Nle-cyclo(-Asp-His-D-Phe(4-Cl)-Arg-Trp-Lys)-OH is a representative example of a peptide of structural formula III.

In another embodiment the invention provides a cyclic peptide of structural formula IV:

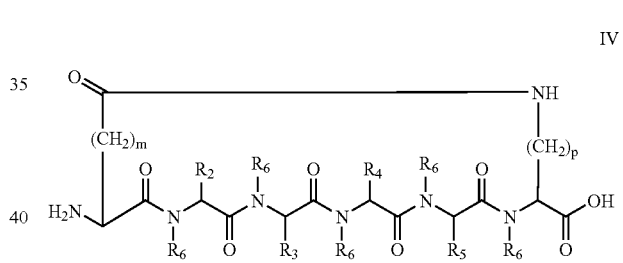

or a pharmaceutically acceptable salt thereof.

In cyclic peptides of structural formula IV, $R_2$, $R_3$, $R_4$, $R_5$, $R_6$, m and p are as defined for structural formula I. The cyclic peptide Cyclo(-Asp-His-D-Phe-Arg-Trp-Lys)-OH is a representative example of a peptide of structural formula IV.

In another embodiment the invention provides a cyclic peptide of structural formula V:

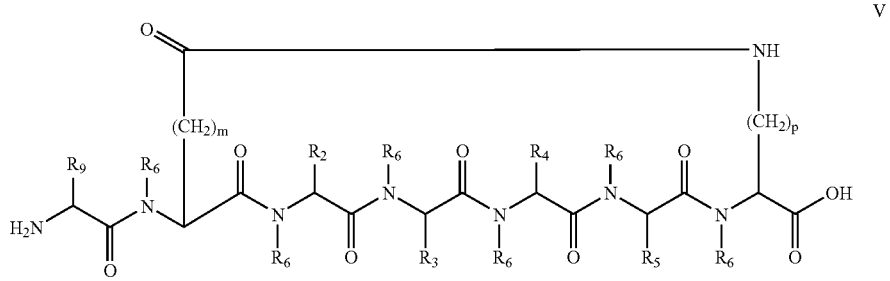

or a pharmaceutically acceptable salt thereof.

In cyclic peptides of structural formula V, $R_2$, $R_3$, $R_4$, $R_5$, $R_6$, m and p are as defined for structural formula I, and $R_9$ is a $C_1$ to $C_6$ aliphatic linear or branched chain, including $CH_3$, or an aromatic amino acid side chain moiety. The cyclic peptide Nle-cyclo(-Asp-His-D-Phe-Arg-Trp-Lys)-OH is a representative example of a cyclic peptide of structural formula V.

In another embodiment the invention provides a cyclic peptide of structural formula VI:

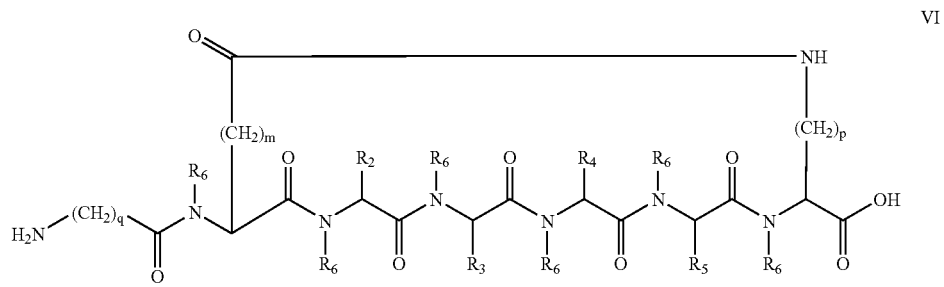

VI or a pharmaceutically acceptable salt thereof.

In cyclic peptides of structural formula $V_1$, $R_2$, $R_3$, $R_4$, $R_5$, $R_6$, m and p are as defined for structural formula I, and q is 1 to 18. The cyclic peptide Ahx-cyclo(-Asp-His-D-Phe-Arg-Trp-Lys)-OH is a representative example of a cyclic peptide of structural formula VI.

In another embodiment, the invention provides a cyclic peptide of structural formula VII:

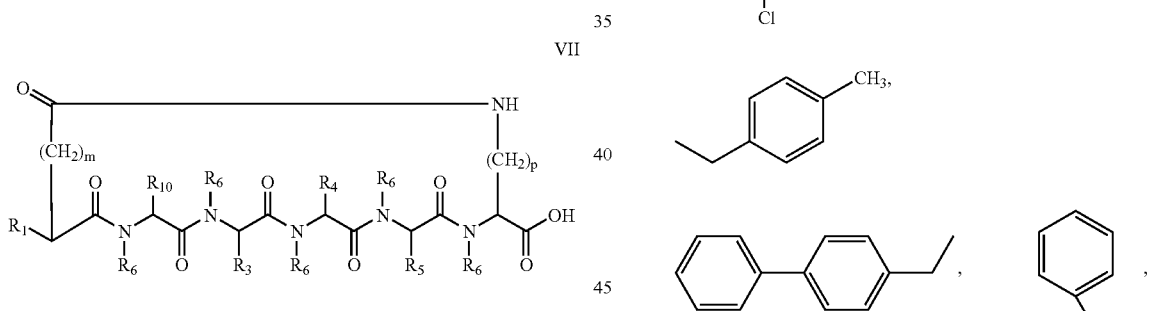

VII or a pharmaceutically acceptable salt thereof.

In cyclic peptides of structural formula VII, $R_1$, $R_3$, $R_4$, $R_5$, $R_6$, $R_7$, m and p are as defined for structural formula I, and $R_{10}$ is an amino acid side chain moiety including at least one 6-membered carbocyclic aromatic ring. Optionally the aromatic amino acid side chain moiety is derived from a natural or synthetic L- or D-amino acid, and is an aromatic substituted aryl or heteroaryl side chain. The aromatic ring or rings of the amino acid side chain moiety may be functionalized with one or more halogens or one or more alkyl or aryl groups. The aromatic amino acid side chain moiety is preferably selected from the following:

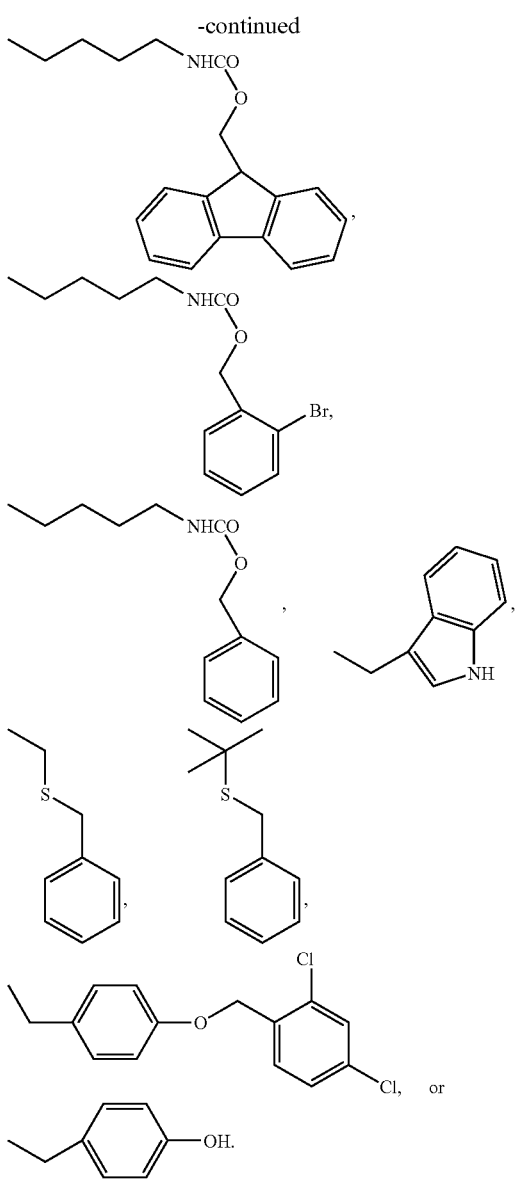

The cyclic peptides Ac-Nle-cyclo(-Asp-Phe-D-Phe-Arg-Trp-Lys)-OH, Ac-Nle-cyclo(-Asp-Trp-D-Phe-Arg-Trp-Lys)-OH, and Ac-Nle-cyclo(-Asp-Tyr-D-Phe-Arg-Trp-Lys)-OH are representative examples of cyclic peptides of structural formula VII.

In another embodiment, the invention provides a cyclic peptide of structural formula VIII:

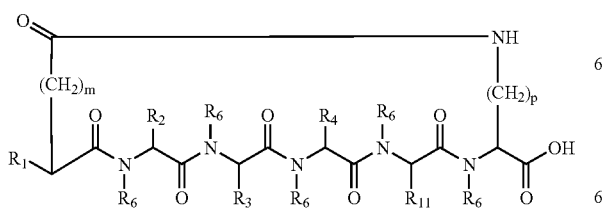

VIII or a pharmaceutically acceptable salt thereof.

In cyclic peptides of structural formula VIII, $R_1$, $R_2$, $R_3$, $R_4$, $R_6$, $R_7$, m and p are as defined for structural formula I, and $R_{11}$ is an amino acid side chain moiety including at least one 6-membered carbocyclic aromatic ring but not including a ring with a nitrogen ring member. Optionally the aromatic amino acid side chain moiety is derived from a natural or synthetic L- or D-amino acid, and is an aromatic substituted aryl or heteroaryl side chain. The aromatic ring or rings of the amino acid side chain moiety may be functionalized with one or more halogens or one or more alkyl or aryl groups. The aromatic amino acid side chain moiety is preferably selected from the following:

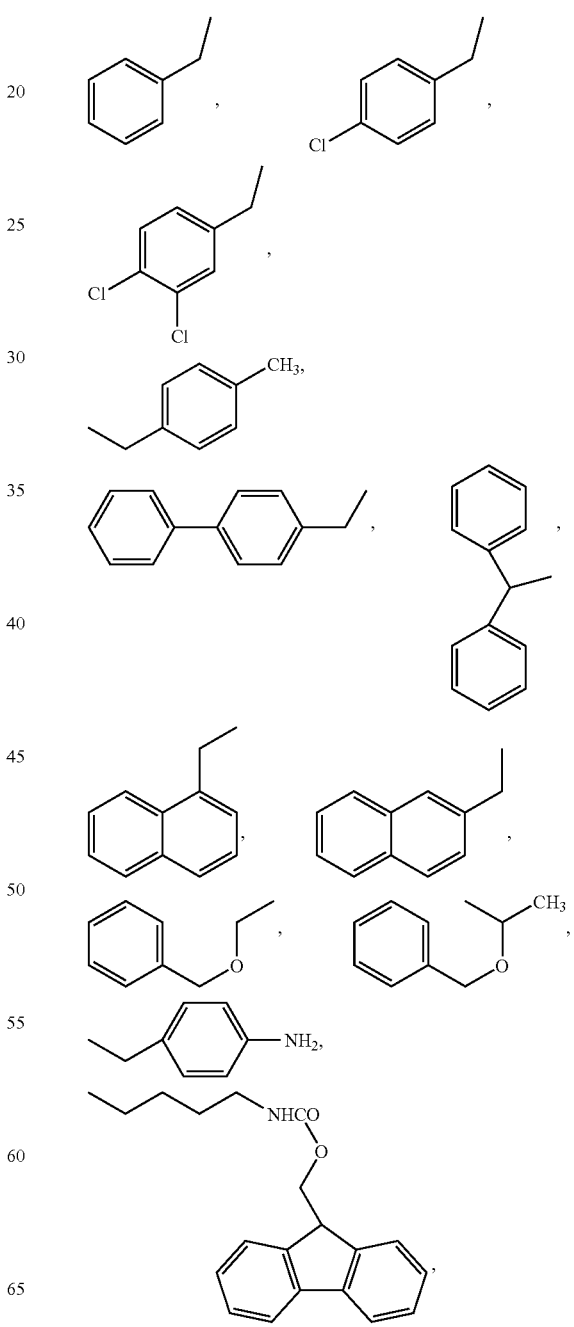

-continued

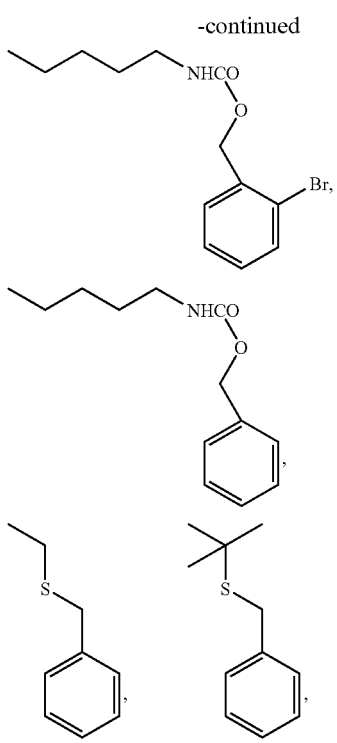

In another embodiment the invention provides a cyclic peptide of structural formula IX:

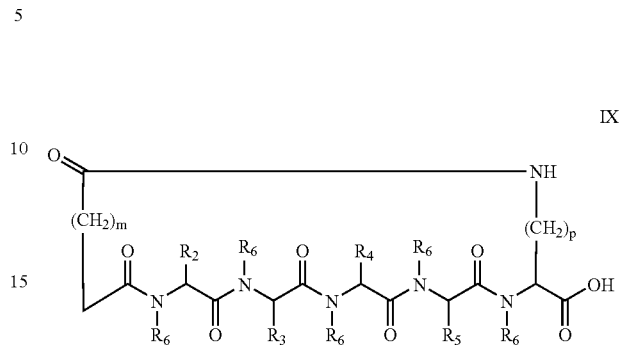

or a pharmaceutically acceptable salt thereof.

In cyclic peptides of structural formula IX, $R_2$, $R_3$, $R_4$, $R_5$, $R_6$, m and p are as defined for structural formula I. The cyclic peptide Cyclo(-Succ-His-D-Phe-Arg-Trp-Lys)-OH is a representative example of a peptide of structural formula IX.

In yet another embodiment the invention provides a cyclic peptide of structural formula X:

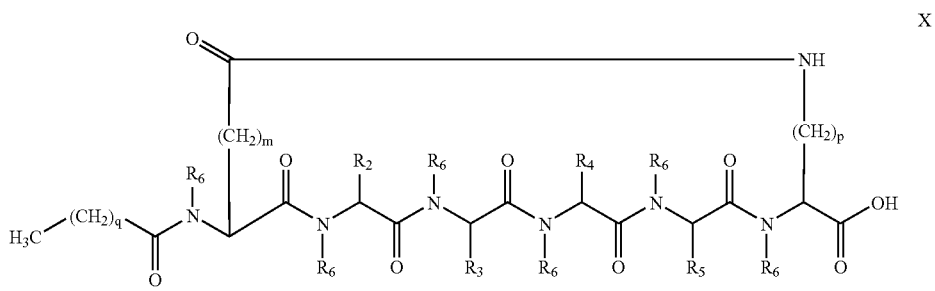

or a pharmaceutically acceptable salt thereof.

In cyclic peptides of structural formula X, $R_2$, $R_3$, $R_4$, $R_5$, $R_6$, m and p are as defined for structural formula I, and q is 0 to 18. The cyclic peptide Heptanoyl-cyclo(-Asp-His-D-Phe-Arg-Trp-Lys)-OH is a representative example of a cyclic peptide of structural formula X.

Peptides of the foregoing formulas may contain one or more asymmetric centers and can thus occur as racemates and racemic mixtures, single enantiomers, diastereomeric mixtures and individual diastereomers. The present invention includes all such isomeric forms of the cyclic peptides the foregoing formulas. Certain of the cyclic peptides of the foregoing formulas contain one or more alkenes, and thus contain olefinic double bonds, and the formulas are meant to include both E and Z geometric isomers where relevant. Other cyclic peptides of the foregoing formulas may exist as tautomers, such as keto-enol tautomers. The individual tautomers as well as mixtures thereof are included with the definition of the formulas.

Cyclic peptides of the foregoing formulas may be separated into their individual diastereoisomers by any means -continued The cyclic peptides Ac-Nle-cyclo(-Asp-His-D-Phe-Arg-Nal 1-Lys)-OH and Ac-Nle-cyclo(-Asp-His-D-Phe-Arg-Bip-Lys)-OH are representative examples of cyclic peptides of structural formula VIII.

known in the art, including but not limited to fractional crystallization from a suitable solvent, such as methanol or ethyl acetate or a mixture thereof, or by chiral chromatography using an optically active stationary phase. It is also possible to synthesize a specific diastereoisomer of a cyclic peptide of any of the foregoing formulas by stereospecific synthesis using optically pure starting materials or reagents of known configuration. In a preferred embodiment, the cyclic peptides of the foregoing formulas are synthesized using reagents of known configurations, and accordingly have a specific diastereoisomeric form.

In a preferred embodiment, the cyclic peptide is one of the following

Ac-Nle-cyclo(-Asp-D-His-D-Phe-Arg-Trp-Lys)-OH
Ac-Nle-cyclo(-Asp-His-Phe-Arg-Trp-Lys)-OH (SEQ ID NO:2)
Ac-Nle-cyclo(-Asp-Phe-D-Phe-Arg-Trp-Lys)-OH
Ac-Nle-cyclo(-Asp-His-D-Phe-Lys-Trp-Lys)-OH
Ac-Nle-cyclo(-Asp-Trp-D-Phe-Arg-Trp-Lys)-OH
Ac-Nle-cyclo(-Asp-His-D-Phe-D-Arg-Trp-Lys)-OH
Ac-Nle-cyclo(-Asp-His-D-Phe-Arg-D-Trp-Lys)-OH
Ahx-cyclo(-Asp-His-D-Phe-Arg-Trp-Lys)-OH
Ac-Nle-cyclo(-Asp-Tyr-D-Phe-Arg-Trp-Lys)-OH
Ac-Nle-cyclo(-Asp-His-D-Phe(4-Cl)-Arg-Trp-Lys)-OH
Ac-Nle-cyclo(-Asp-His-D-Phe-Orn-Trp-Lys)-OH
Nle-cyclo(-Asp-His-D-Phe-Arg-Trp-Lys)-OH
Ac-Nle-cyclo(-Asp-His-D-Phe-Arg-Nal 1-Lys)-OH
Ac-Nle-cyclo(-Asp-His-D-Phe-Arg-Bip-Lys)-OH
Cyclo(-Succ-His-D-Phe-Arg-Trp-Lys)-OH The invention further includes pharmaceutical compositions, including a cyclic peptide of this invention and a pharmaceutically acceptable carrier. The pharmaceutically acceptable carrier may be a buffered aqueous carrier, and preferably a saline or citrate buffered carrier.

The invention further includes methods for treatment of sexual dysfunction, including treating erectile dysfunction in males or female sexual dysfunction, the methods including administration of a therapeutically effective amount of a composition including a cyclic peptide with a C-terminus —OH group and containing a sequence including His-Phe-Arg-Trp (SEQ ID NO:1), His-D-Phe-Arg-Trp, a homolog of His-Phe-Arg-Trp (SEQ ID NO:1) or a homolog of His-D-Phe-Arg-Trp. In an alternative embodiment, the method further includes administration of the free acid cyclic peptide in combination with a therapeutically effective amount of a second sexual dysfunction pharmaceutical agent. The second sexual dysfunction pharmaceutical agent can include an MC4-R agonist, which may be a peptide or a small molecule, a PDE-5 inhibitor, an alpha-andrenergic receptor antagonist, a sexual response related hormone, such as testosterone in males or estrogen in females, or other compounds or devices useful in treatment of sexual dysfunction. The present invention also encompasses pharmaceutical compositions useful in the foregoing method of the present invention, such as compositions including a peptide of this invention and one or more second sexual dysfunction pharmaceutical agents, as well as a method of manufacture of a medicament useful to treat sexual dysfunction.

The peptides of this invention, and pharmaceutical compositions of this invention, may be used for stimulating sexual response in a mammal. The invention thus also includes a method for stimulating sexual response in a mammal, in which a therapeutically effective amount of a pharmaceutical composition is administered. The mammal may be male or female. In this method, the composition can also include a pharmaceutically acceptable carrier. The peptide or pharmaceutical composition may be administered by any means known in the art, including administration by injection, administration through mucous membranes, buccal administration, oral administration, dermal administration, urethral administration, vaginal administration, inhalation administration and nasal administration. In a preferred embodiment, administration is by oral administration, including sublingual administration, of a specified amount of a formulation including an appropriate carrier, bulking agent and the like.

A primary object of the present invention is to provide a C-terminus free acid melanocortin receptor-specific pharmaceutical for use in treatment of sexual dysfunction.

A second object is to provide a C-terminus free acid peptide-based melanocortin receptor-specific pharmaceutical for use in treatment of male sexual dysfunction, including erectile dysfunction.

Yet another object is to provide a C-terminus free acid peptide-based melanocortin receptor-specific pharmaceutical for use in treatment of female sexual dysfunction.

Yet another object is to provide a C-terminus free acid peptide-based melanocortin receptor-specific pharmaceutical for use in treatment of sexual dysfunction with substantially reduced incidence of undesirable side effects.

Yet another object is to provide a C-terminus free acid cyclic peptide wherein utility for treatment of sexual dysfunction is independent of specificity for any given melanocortin receptor.

An advantage of the present invention is that it provides a C-terminus free acid cyclic peptide-based melanocortin receptor-specific pharmaceutical for use in treatment of sexual dysfunction which is efficacious at low doses.

Another advantage of the present invention is that it provides a C-terminus free acid cyclic peptide-based melanocortin receptor-specific pharmaceutical that is effective over a significant dose range, without deleterious side effects.

Yet another advantage of the present invention is that it provides a C-terminus free acid cyclic peptide-based melanocortin receptor-specific pharmaceutical for use in treatment of sexual dysfunction which is rapidly pharmaceutically active following administration.

Yet another advantage of the present invention is that it provides a C-terminus free acid cyclic peptide-based melanocortin receptor-specific pharmaceutical for use in treatment of sexual dysfunction which, because of increased efficacy at low doses, may be administered by delivery systems other than art conventional intravenous, subcutaneous or intramuscular injection, including but not limited to oral delivery systems, nasal delivery systems and mucous membrane delivery systems.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS (BEST MODES FOR CARRYING OUT THE INVENTION)

Definitions

The "peptides" of this invention can be (a) naturally-occurring, (b) produced by chemical synthesis, (c) produced by recombinant DNA technology, (d) produced by biochemical or enzymatic fragmentation of larger molecules, (e) produced by methods resulting from a combination of methods (a) through (d), or (f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" includes dimers or multimers of peptides. A "manufactured" peptide includes a peptide produced by chemical synthesis, recombinant DNA technology, biochemical or enzymatic fragmentation of larger molecules, combinations of the foregoing or, in general, a peptide made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

Homologs of the peptide include those sequences with a single amino acid substitution at any location. In one embodiment of the invention, the substitution is made by any of the naturally occurring amino acids or unnaturally occurring amino acids. In a preferred embodiment the substitution is made by Phe, Lys, Trp, Tyr, Phe(4-Cl), Orn, Nal 1, or Bip. Homologs of the peptide may also include those sequences where one amino acid with an aromatic ring has been substituted for another amino acid with a different aromatic ring. An example of this substitution would be replacing a Phe residue with a Trp residue. Homologs of the peptide may also include those sequences where an amino acid with a charged side chain is replaced by another amino acid with or without a charged side chain. Examples of this include, without limitation, replacing an Arg residue (positively charged side chain) with a Lys (positively charged side chain) or replacing a His (positively charged side chain) with a Phe (nonpolar side chain).

The "amino acids" used in this invention, and the term as used in the specification and claims, include the known naturally occurring protein amino acids, which are referred to by their common three letter abbreviation. See generally *Synthetic Peptides: A User's Guide*, G A Grant, editor, W.H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F. and Kazmierski W., Emerging approaches in the molecular design of receptor-selective peptide ligands—conformational, topographical and dynamic considerations. *Biochem J* 268:249–262 (1990); and Toniolo C., Conformationally restricted peptides through short-range cyclizations. *Int J Peptide Protein Res* 35:287–300 (1990); the teachings of all of which are incorporated herein by reference. In addition, the following abbreviations setting forth amino acids, constituent portions thereof, reagents used in synthesis thereof, and the like, have the meanings giving:

| | |
|---|---|
| Abu | gamma-amino butyric acid |
| 2-Abz | 2-amino benzoic acid |
| 3-Abz | 3-amino benzoic acid |
| 4-Abz | 4-amino benzoic acid |
| Achc | 1-amino-cyclohexane-1-carboxylic acid |
| Acpc | 1-amino-cyclopropane-1-carboxylic acid |
| 12-Ado | 12-amino dodecanoic acid |
| Aic | 2-aminoindane-2-carboxylic acid |
| Ahx | 6-amino hexanoic acid |
| 8-Aoc | 8-amino octanoic acid |
| aminoheptanoyl | $NH_2-(CH_2)_6CO-$ |
| Arg(Mtr) | $N^G$-4-methoxy-2,3,6-trimethylbenzenesulfonyl-arginine |
| Arg(Me) | $N^G$-methyl-arginine |
| Arg(NO$_2$) | $N^G$-nitro-arginine |
| Arg(Pbf) | $N^G$-pentamethyldihydrobenzofuransulfonyl-arginine |
| Arg(Pmc) | $N^G$-pentamethylchromansulfonyl-arginine |
| Arg(Tos) | $N^G$-tosyl-arginine |
| Asp(anilino) | beta-anilino-aspartic acid |
| Asp(3-Cl-anilino) | beta-(3-chloro-anilino)-aspartic acid |
| Asp(3,5-diCl-anilino) | beta-(3,5-dichloro anilino)-aspartic acid |
| D/L Atc | (D,L)-2-aminotetralin-2-carboxylic acid |
| Bip | biphenylalanine |
| Bz | benzoyl |
| Cha | cyclohexylalanine |
| Chg | cyclohexylglycine |
| Dip | 3,3-diphenylalanine |
| Et | ethyl |
| Harg | homoarginine |
| Hphe | homophenylalanine |

-continued

| | |
|---|---|
| Lys(Z) | N-epsilon-benzyloxycarbonyl-lysine |
| Me | methyl |
| Nal 1 | 3-(1-naphthyl)alanine |
| Nal 2 | 3-(2-naphthyl)alanine |
| Phg | phenylglycine |
| pF-Phe | para-fluoro-phenylalanine |
| Phe(4-Br) | 4-bromo-phenylalanine |
| Phe(4-CF$_3$) | 4-trifluoromethyl-phenylalanine |
| Phe(4-Cl) | 4-chloro-phenylalanine |
| Phe(2-Cl) | 2-chloro-phenylalanine |
| Phe(2,4-diCl) | 2,4,-dichloro-phenylalanine |
| Phe(3,4-diCl) | 3,4-dichloro-phenylalanine |
| Phe(3,4-diF) | 3,4-difluoro-phenylalanine |
| Phe(4-I) | 4-iodo-phenylalanine |
| Phe(3,4-di-OMe) | 3,4,-dimethoxy-phenylalanine |
| Phe(4-Me) | 4-methyl-phenylalanine |
| Phe(4-NO$_2$) | 4-nitro-phenylalanine |
| Qal(2') | beta-(2-quinolyl)-alanine |
| Sal | 3-styrylalanine |
| Ser(Bzl) | O-benzyl-serine |
| Succ | Succinyl |
| TFA | trifluoroacetyl |
| Tic | 1,2,3,4-tetrahydroisoquinoline-3-carboxylic acid |
| Tle | tert-butylalanine |

In the listing of peptides according to the present invention, conventional amino acid residues have their conventional meaning as given in Chapter 2400 of the *Manual of Patent Examining Procedure*, 7$^{th}$ Ed. Thus, "Nle" is norleucine; "Asp" is aspartic acid; "His" is histidine; "D-Phe" is "Arg" is arginine; "Trp" is tryptophan; "Lys" is lysine; "Gly" is glycine; "Pro" is proline; "Tyr" is tyrosine, and "Ser" is serine. "Ac" refers to a peptide or amino acid sequence that is acetylated.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue".

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —R$^a$R$^b$ where R$^a$ is an alkylene (a bivalent alkyl) group and R$^b$ is an aryl group as defined above. Examples of aralkyl groups include benzyl, phenylethyl, 3-(3-chlorophenyl)-2-methylpentyl, and the like. The term "aliphatic" includes compounds with hydrocarbon chains, such as for example alkanes, alkenes, alkynes, and derivatives thereof.

The term "acyl" includes a group RCO—, where R is an organic group. An example is the acetyl group CH$_3$CO—.

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH$_2$), such as for example methylamide, ethylamide, propylamide, and the like.

An "imide" includes compounds containing an imido group (—CO.NH.CO—).

An "amine" includes compounds that contain an amino group (—NH$_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —CF$_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound or peptide of the present invention and a pharmaceutically acceptable carrier.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by a melanocortin receptor agonist agent.

By "binding affinity" is meant the ability of a compound or drug to bind to its biological target.

Cyclic Peptides of the Invention

In one embodiment the invention provides deamidated α-MSH cyclic peptides, which are cyclic peptides that include the core α-MSH sequence His-Phe-Arg-Trp (SEQ ID NO:1), His-D-Phe-Arg-Trp, or homologs or analogs of either of the foregoing, in which the peptide is deamidated, which is to say that it does not include an —NH₂ group at the C-terminus. In a preferred embodiment, the deamidated α-MSH cyclic peptides of this invention have an —OH group at the C-terminus, and are thus a free acid form of cyclic peptide.

In another aspect, the invention provides certain deamidated cyclic peptides, specific for one or more melanocortin receptors, and which in some embodiments are an agonist with respect to such receptor or receptors. However, the peptides of this invention need not be agonists, and need not have significant specificity for any one given melanocortin receptor. In general, there is no rank order correlation between affinity for a given receptor, such as MC4-R, measured by either competitive inhibition with α-MSH or an analog, such as NDP-MSH, including $K_i$ value, and effectiveness for treatment of sexual dysfunction. Such peptides can preferably be employed in the treatment of sexual dysfunction, and may be characterized in part as inducing an erectile response in mammalian males, including but not limited to, rodents.

Homologs of the cyclic peptide include those sequences with a single amino acid substitution at any location. In one embodiment of the invention, the substitution is made by any of the naturally occurring amino acids or unnaturally occurring amino acids. In a preferred embodiment the substitution is made by Phe, Lys, Trp, Tyr, Phe(4-Cl), Orn, Nal 1, or Bip. Homologs of the peptide may also include those sequences where one amino acid with an aromatic ring has been substituted for another amino acid with a different aromatic ring. An example of this substitution would be replacing a Phe residue with a Trp residue. Homologs of the peptide may also include those sequences where an amino acid with a charged side chain is replaced by another amino acid with or without a charged side chain. Examples of this include, without limitation, replacing an Arg residue (positively charged side chain) with a Lys (positively charged side chain) or replacing a His (positively charged side chain) with a Phe (nonpolar side chain).

The peptide is a cyclic peptide. A cyclic peptide can be obtained by inducing the formation of a covalent bond between an amino group at the N-terminus of the peptide, if provided, and a carboxyl group at the C-terminus, if provided. A cyclic peptide can also be obtained by forming a covalent bond between a terminal reactive group and a reactive amino acid side chain moiety, or between two reactive amino acid side chain moieties. One skilled in the art would know that the means by which a given peptide is made cyclic is determined by the reactive groups present in the peptide and the desired characteristic of the peptide. In a preferred embodiment, the peptide is made cyclic between two reactive amino acid side chain moieties by means which do not involve a disulfide bridge.

Pharmaceutical Compositions of the Invention. The pharmaceutical compositions of the invention may further be defined as a composition for treating sexual dysfunction in a mammal which includes a cyclic peptide or a pharmaceutically acceptable salt thereof of the formula XI:

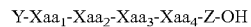

$$Y\text{-}Xaa_1\text{-}Xaa_2\text{-}Xaa_3\text{-}Xaa_4\text{-}Z\text{-}OH \qquad \qquad XI$$

wherein Y includes from one to about three L- or D-amino acid residues, optionally with an N-terminus acetyl group; Z includes from one to about three L- or D-amino acid residues with a C-terminus —OH group; $Xaa_1$, $Xaa_2$, and $Xaa_4$ are each independently an L- or D-amino acid with a side chain consisting of H or containing a $C_1$ to $C_6$ aliphatic linear or branched chain, including $CH_3$, or an aromatic amino acid side chain moiety, on the proviso that at least one of $Xaa_2$ and $Xaa_4$ is not H or a $C_1$ to $C_6$ aliphatic linear or branched chain; $Xaa_3$ is an L- or D-amino acid with a $C_1$ to $C_6$ linear or branched chain amino acid side chain or a neutral hydrogen bonding or positively charged amino acid side chain; and wherein the peptide is cyclized through formation of a covalent bond, other than an —S—S— bond, between an amino group at the N-terminus of the peptide, if provided, and a reactive amino acid side chain moiety of an amino acid residue comprising Z, or between a reactive amino acid side chain moiety of an amino acid residue comprising Y and a reactive amino acid side chain moiety of an amino acid residue comprising Z.

It may thus be seen that the minimum construct of formula XI includes six amino acid residues, and that the maximum construct includes about ten amino acid residues. The construct of formula XI may further include structures defined herein as an amino acid residue, such as for example Y can include an N-terminus aminoheptanoyl.

In a preferred embodiment, the peptide is cyclized through a reactive amino acid side chain moiety of an amino acid residue comprising Y and a reactive amino acid side chain moiety of an amino acid residue comprising Z. The reactive amino acid side chain moiety of Y preferably includes a terminal —COOH group and the reactive amino acid side chain moiety of Z preferably includes a $C_1$ to $C_5$ aliphatic linear chain with a terminal —$NH_2$ group. In one embodiment, the amino acid residue of Y with a reactive amino acid side chain moiety is Asp or Succ, and the amino acid residue of Z with a reactive amino acid side chain moiety is Lys.

In a preferred embodiment, Y includes an amino acid residue with an N-terminus acetyl group. In one embodiment, the N-terminus amino acid residue is Ac-Nle-.

It may thus be seen that in one embodiment, the invention is characterized, in part, as a cyclic peptide of from six to about ten amino acid residues, wherein $Xaa_1$-$Xaa_2$-$Xaa_3$-$Xaa_4$ is His-Phe-Arg-Trp or amino acid residues including mimetics or homologs of any one or more of each of His, Phe, Arg, or Trp, including without limitation all known derivatives and isomers of each of His, Phe, Arg and Trp. Derivatives of His include, by way of example and not limitation, L-or D-isomers of His, α-methyl-His, or $N^{im}$-methyl-His. Derivatives of Phe include, by way of example and not limitation, L- or D-isomers of Phe, pF-Phe, Phe(4-Br), Phe(4-$CF_3$), Phe(4-Cl), Phe(2-Cl), Phe(2,4-diCl), Phe(3,4-diCl), Phe(3,4-diF), Phe(4-l), Phe(3,4-di-OMe), Phe(4-Me), or Phe(4-$NO_2$), among other variants of Phe. Derivatives of Arg include, by way of example and not limitation, L- or D-isomers of Arg, Arg($NO_2$), Arg(Tos), Arg(Pbf), Arg(Mtr), Arg(Me), and Arg(Pmc), among other variants of Arg. Derivatives of Trp include, by way of example and not limitation, L-or D-isomers of Trp, 5-methoxy-Trp, 5-hydroxy-Trp, 2-mercapto-Trp, or 2-mercaptoacetyl-Trp.

In a preferred embodiment, $Xaa_1$ includes His, Phe, Trp, or Tyr. Here and elsewhere, an amino acid residue specific formula reference, such as for example $Xaa_1$, is said to "include" or "comprise" an amino acid, such as for example Phe, when such amino acid residue is Phe or a derivative or isomer thereof, including a derivative of an amino acid side chain moiety as defined herein. Thus, for example, Phe includes L- or D-isomers of Phe, pF-Phe, Phe(4-Br), Phe (4-$CF_3$), Phe(4-Cl), Phe(2-Cl), Phe(2,4-diCl), Phe(3,4-diCl), Phe(3,4-diF), Phe(4-l), Phe(3,4-di-OMe), Phe(4 -Me), and Phe(4-$NO_2$), among other derivatives of Phe.

In a preferred embodiment, $Xaa_2$ includes Phe, Hphe, Phg, including L- or D-isomers of Phe, pF-Phe, Phe(4-Br), Phe(4-$CF_3$), Phe(4-Cl), Phe(2-Cl), Phe(2,4-diCl), Phe(3,4-diCl), Phe(3,4-diF), Phe(4-l), Phe(3,4-di-OMe), Phe(4-Me), Phe(4-$NO_2$), and similar ring substituted derivatives of Phg and Hphe.

In a preferred embodiment, $Xaa_3$ includes Arg, including L- or D-isomers of Arg, Harg, Arg($NO_2$), Arg(Tos), Arg (Pbf), Arg(Mtr), Arg(Me), Arg(Pmc), Harg($NO_2$), Harg (Tos), Harg(Pbf), Harg(Mtr), Harg(Me), Harg(Pmc), among other variants of Arg. Alternatively $Xaa_3$ may include Cit, Lys or Orn.

In a preferred embodiment, $Xaa_4$ includes Trp, Nal 1, Nal 2, Sal, Bip, Qal, or Dip, including L- or D-isomers of each of the foregoing.

In a preferred embodiment, both $Xaa_2$ and $Xaa_4$ are amino acid residues that include aromatic amino acid side chain moieties. Optionally the aromatic amino acid side chain moiety is derived from a natural or synthetic L- or D-amino acid, and is an aromatic substituted aryl or heteroaryl side chain. The aromatic ring or rings of the amino acid side chain moiety may be functionalized with one or more halogens or one or more alkyl or aryl groups. The aromatic amino acid side chain moiety is preferably selected from the following:

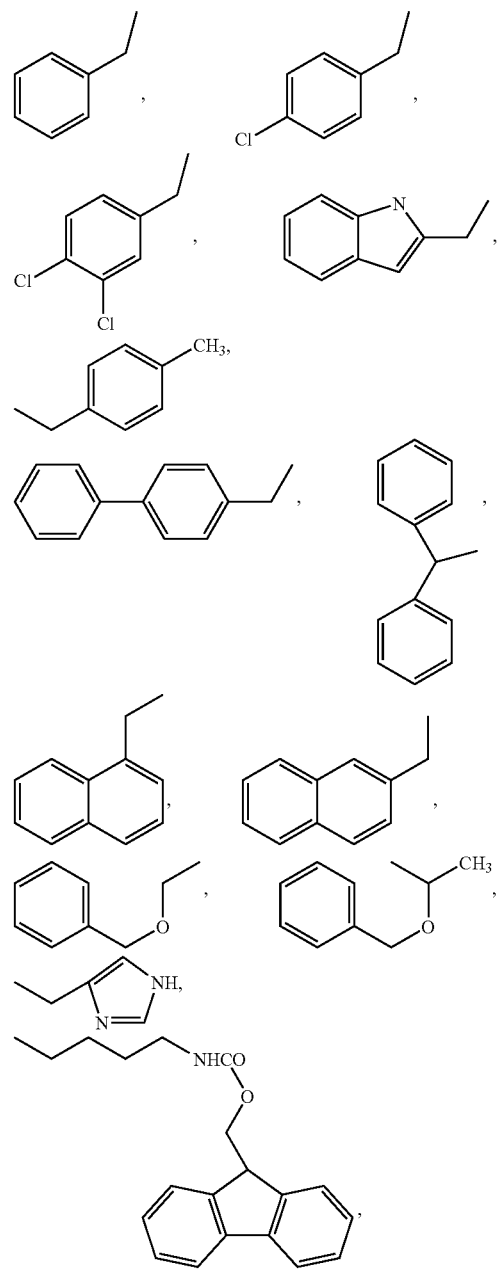

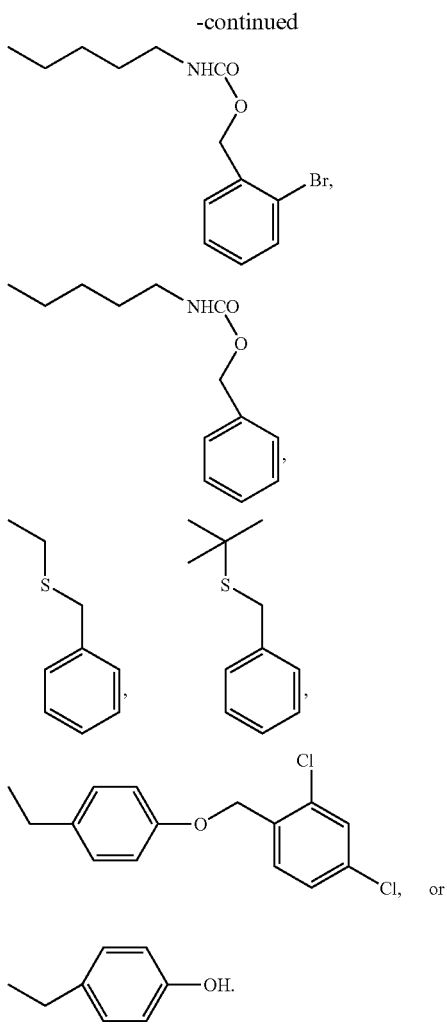
In an alternative embodiment, the amino acid residue at the Xaa$_2$ and Xaa$_4$ positions, or both, may be a derivatized, modified, synthetic or unnatural amino acid, such as by way of example only any of the following, which may further include isomers of the following:
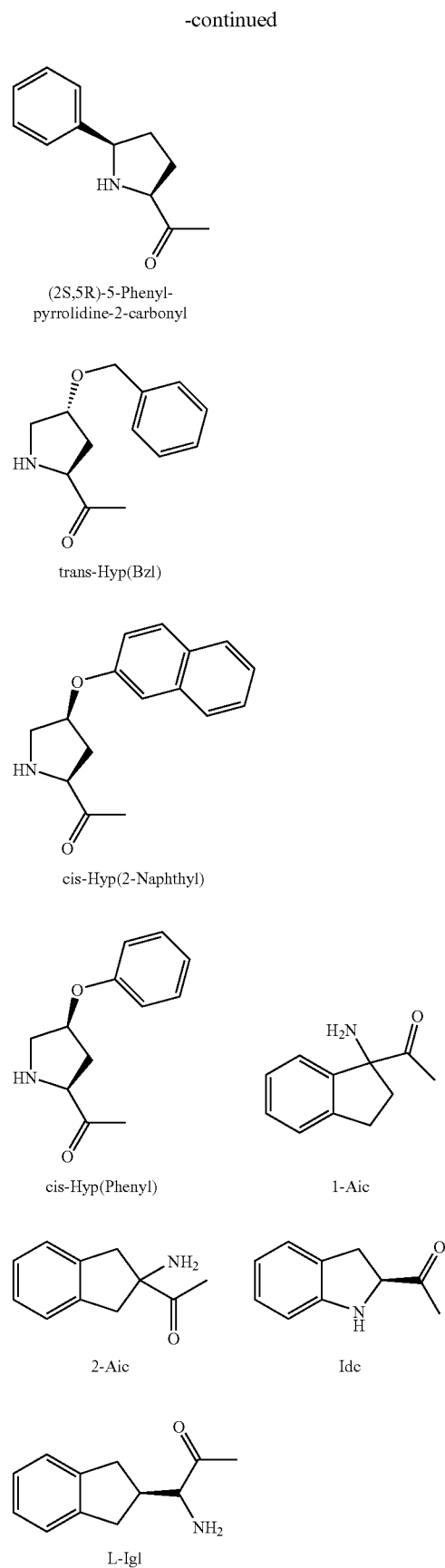

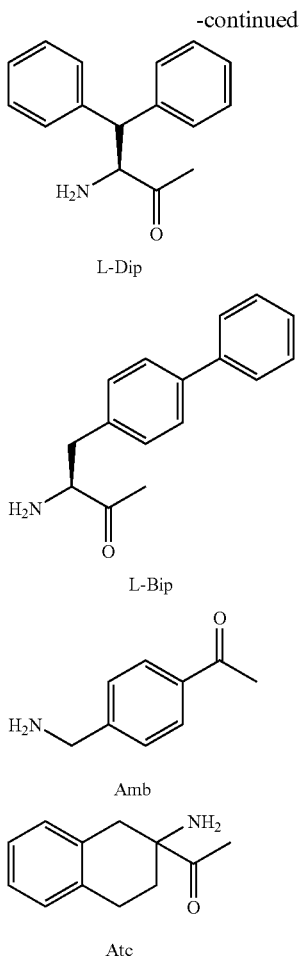

L-Dip

L-Bip

Amb

Atc

In a preferred embodiment, $Xaa_3$ is an L- or D-amino acid with neutral hydrogen bonding or positively charged amino acid side chain moiety that is an aliphatic or aromatic amino acid side chain moiety derived from a natural or synthetic L- or D-amino acid, wherein the moiety includes at least one nitrogen-containing group, including an amide, imide, amine, guanidine, urea, urethane, or nitrile. The $Xaa_3$ L- or D-amino acid with a nitrogen-containing amino acid side chain moiety is preferably selected from the following:

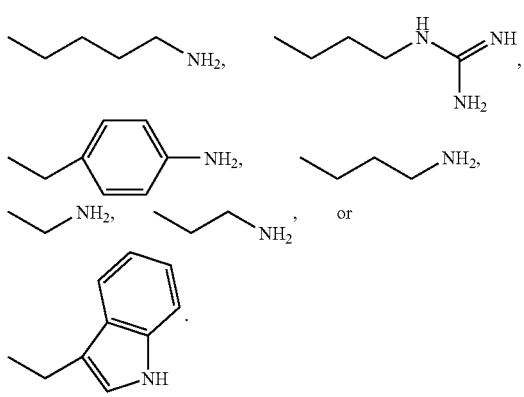

The $Xaa_3$ L- or D-amino acid with a neutral aliphatic amino acid side chain moiety, wherein the side chain includes hydrogen donors and/or acceptors, is preferably be selected from the following:

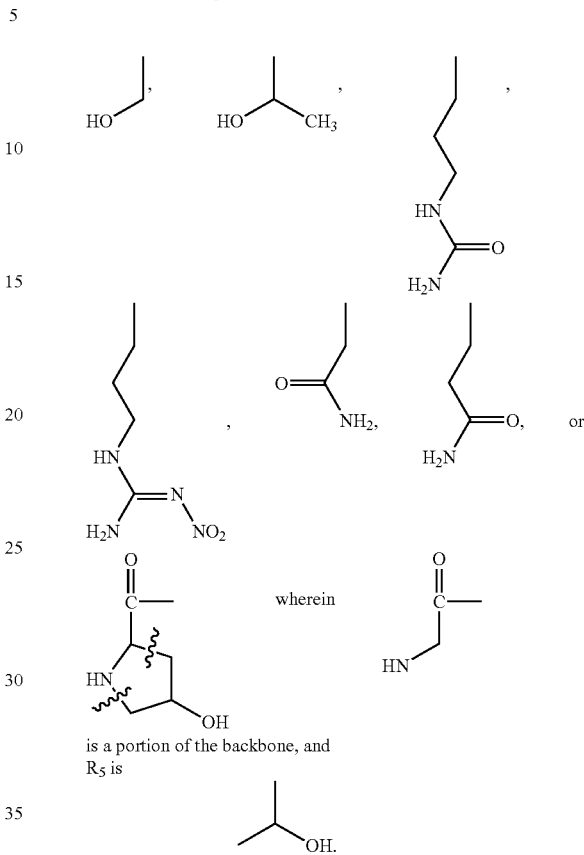

is a portion of the backbone, and $R_5$ is

The cyclic peptides of this invention may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a cyclic peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Peptide Synthesis. The cyclic peptides of this invention may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected. In a preferred conventional procedure, the cyclic peptides of this invention may be synthesized by solid-phase synthesis and purified according to methods known in the art. Any of a number of well-known procedures utilizing a variety of resins and reagents may be used to prepare the peptides of this invention.

The process for synthesizing the cyclic peptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such a method the synthesis of peptides of the invention can be carried out by sequentially incorporating the desired amino acid residues one at a time into the growing peptide chain according to the general principles of solid phase methods. These methods are disclosed in numerous references, including, Merrifield, R. B., Solid phase synthesis (Nobel lecture). *Angew Chem* 24:799–810 (1985) and Barany et al., *The Peptides, Analysis, Synthesis and Biology*, Vol. 2, Gross, E. and Meienhofer, J., Eds. Academic Press 1–284 (1980).

In chemical syntheses of peptides, reactive side chain groups of the various amino acid residues are protected with suitable protecting groups, which prevent a chemical reaction from occurring at that site until the protecting group is removed. Usually also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods. Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, and Boc. Pmc is a preferred protecting group for Arg.

The peptides of the invention described herein were prepared using solid phase synthesis, in most cases by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis was commenced from the C-terminal end of the peptide by coupling a protected alpha amino acid to a suitable resin. Such a starting material can be prepared by attaching an alpha amino-protected amino acid by an ester linkage to a p-benzyloxybenzyl alcohol (Wang) resin or a 2-chlorotrityl chloride resin, by an amide bond between an Fmoc-Linker, such as p-[(R, S)-α-[1-(9H-fluoren-9-y)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20–40% v/v) in DMF may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Methods for N-terminus modification, such as acetylation, or C-terminus modification, such as amidation, are well known in the art. Similarly, methods for modifying side chains of amino acids are well known to those skilled in the art of peptide synthesis. The choice of modifications made to reactive groups present on the peptide will be determined, in part, by the characteristics that are desired in the peptide.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(7-aza-1H-benzotriazol-1-yl)-1,1,3,3-tetramethyluronium tetrafluoroborate (TATU), 2-(2-oxo-1 (2H)-pyridyl)-1,1,3,3-tetramethyluronium tetrafluoroborate (TBTU) or N, N'-dicyclohexylcarbodiimide/1-hydroxybenzotriazole (DCCl/HOBt). Coupling is conventionally initiated by use of a suitable base, such as N,N-diisopropylethylamine (DIPEA), sym-collidine or N-methylmorpholine (NMM).

Following cleavage of peptides from the solid phase following their synthesis, the peptide can be purified by any number of methods, such as reverse phase high performance liquid chromatography (RP-HPLC), using a suitable column, such as a C-18 column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Melanocortin Receptor Binding Assays. The cyclic peptides of this invention are characterized, in part, in that they bind to selected melanocortin receptors, and specifically MC4-R and MC3-R, as determined by competitive inhibition binding assay using α-MSH. Thus the cyclic peptide inhibits the binding of α-MSH or an α-MSH analog to MC4-R. NDP-MSH is one example of a α-MSH analog. Similarly the cyclic peptide inhibits the binding of α-MSH or a α-MSH analog to MC3-R. The peptide is further characterized as a melanocortin receptor agonist, and specifically a MC4-R agonist and a MC3-R agonist.

Competitive inhibition binding assays were conducted using membranes prepared from hMC3-R, hMC4-R, hMC5-R, and B-16 mouse melanoma cells (containing MC1-R) using 0.4 nM $^{125}$I-NDP-MSH (0.2 nM for MC1-R) (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the peptides of this invention, for determining inhibition of the binding of $^{125}$I-NDP-MSH to its receptor. Non-specific binding was measured by complete inhibition of binding of $^{125}$I-NDP-MSH in the assay in the presence of 1 μM α-MSH. Incubation was for 90 minutes at 37° C., after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in the presence of peptides of this invention were normalized with respect to 100% specific binding to determine the percent inhibition of $^{125}$I-NDP-MSH binding. Each assay was conducted in triplicate.

A cyclic peptide inhibited α-MSH binding, determined by the percentage binding of $^{125}$I-NDP-MSH, when statistically significant detectable measured inhibition was observed.

Functional assays to determine agonist or antagonist status of a cyclic peptide of the invention may be conducted by any means known in the art. In one method, a cAMP assay is performed. Human MC4-R cells are grown to confluence in 96 well plates (plating approximately 250,000 cells per well). Identical sets of cells in triplicate are treated with 0.2 mM isobutylmethylxanthine (IBMX) and the chosen concentration of the peptide or alternatively the peptide in the presence of 20 nM NDP-MSH. Cells similarly treated but with only 20 nM NDP-MSH serve as positive controls in a volume of 200 μL. A buffer blank, as a negative control, is also included. Incubation is for one hour at 37° C. after which the cells are lysed by the addition of 50 μL of a cell lysis buffer. Total cAMP accumulated in 250 μL of this solution is quantitated using a commercially available low pH cAMP assay kit (Amersham BioSciences) by the procedure specified by the kit supplier. Any peptide showing cAMP accumulation in the same range as or higher than the positive control (buffer blank in the presence of α-MSH) is considered to be an agonist. A peptide showing accumulation in the same range as the negative control (buffer blank in the absence of α-MSH) is ineffective at the test concentration if the result is similar to the positive control where α-MSH is also present in the assay. A peptide showing accumulation in the same range as the negative control is considered to be an antagonist if there is inhibition in cAMP when α-MSH is present in the assay. Similar methods may be employed for MC3-R, using MC3-R cells.

Formulation and Utility

The cyclic peptides and pharmaceutical compositions of this invention can be used for both medical applications and animal husbandry or veterinary applications. Typically, the cyclic peptide or pharmaceutical composition is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Therapeutic Application in Males. The cyclic peptides and pharmaceutical compositions of this invention may be used to treat male sexual dysfunction, including erectile dysfunction or impotence.

Therapeutic Application in Females. The cyclic peptides and pharmaceutical compositions of this invention may be used to treat female sexual dysfunction, including without limitation sexual arousal disorder.

Diagnostic Application. The cyclic peptides of this invention may be used for diagnostic purposes, to diagnose causes of erectile dysfunction in males, or sexual dysfunction in mammals generally. Thus, the cyclic peptides may be administered and the erectile reaction of the patient monitored.

Salt Form of Cyclic Peptides. The cyclic peptides of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of this invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptides of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. The invention provides a pharmaceutical composition that includes a cyclic peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of this invention may be formulated or compounded into pharmaceutical compositions that include at least one cyclic peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of cyclic peptides of this invention administered to a patient will vary between fairly wide ranges depending on the mode of administration, the formulation used, and the response desired.

In practical use, the cyclic peptides of the invention can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another advantageous dosage unit form, sublingual constructs may be employed, such as sheets, wafers, tablets or the like. The active peptides can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Cyclic peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Cyclic peptides may also be administered by transurethral delivery. The formulation for transurethral delivery may contain one or more selected carriers or excipients, such as water, silicone, waxes, petroleum jelly, polyethylene glycol, propylene glycol, liposomes, sugars such as mannitol and lactose, and/or a variety of other materials, with polyethylene glycol and derivatives thereof particularly preferred. Depending on the peptide administered, it may be desirable to incorporate a transurethral permeation enhancer in the urethral dosage form. Examples of suitable transurethral permeation enhancers include dimethylsulfoxide, dimethyl formamide, N,N-dimethylacetamide, decylmethylsulfoxide ($C_{10}MSO$), polyethylene glycol monolaurate, glycerol monolaurate, lecithin, alcohols, such as ethanol, detergents, and the like. Transurethral formulations may additionally include one or more enzyme inhibitors effective to inhibit peptide degrading enzymes which may be present in the urethra. Such enzyme inhibiting compounds may be determined by those skilled in the art by reference to the pertinent literature and/or using routine experimental methods. Additional optional components include excipients, preservatives, such as antioxidants, chelating agents, solubilizing agents, such as surfactants, and the like, as will be appreciated by those skilled in the art of drug formulation preparation and delivery.

Transurethral drug administration can be carried out in a variety of different ways using a variety of urethral dosage forms. For example, the peptide in an appropriate formulation can be introduced into the urethra through a flexible tube, squeeze bottle, pump, or aerosol spray. The peptide may also be contained in coatings, pellets, or suppositories which are absorbed, melted, or bioeroded in the urethra. In certain embodiments, the peptide is included in a coating on the exterior surface of a penile insert.

Cyclic peptides of this invention may also be administered vaginally. The delivery system can be a solid object such as a tampon, tampon-like device, vaginal ring, cup, pessary, tablet, or suppository. Alternatively it can be a composition in the form of a cream, paste, ointment, or gel having a sufficient thickness to maintain prolonged contact with vaginal epithelium. Alternatively, it can be a coating on a suppository wall or a sponge or other absorbent material impregnated with a liquid drug formulation further containing a solution, lotion, or suspension of bioadhesive particles, for example. Any form of drug delivery system which will effectively deliver the peptide to the vaginal endothelium is intended to be included within the scope of this invention.

The cyclic peptides of this invention may be therapeutically applied by means of nasal administration. By "nasal administration" is meant any form of intranasal administration of any of the cyclic peptides of this invention. The peptides may be in an aqueous solution, such as a solution including saline, citrate or other common excipients or preservatives. The peptides may also be in a dry or powder formulation.

In an alternative embodiment, cyclic peptides of this invention may be administered directly into the lung. Intrapulmonary administration may be performed by means of a metered dose inhaler, a device allowing self-administration of a metered bolus of a peptide of this invention when actuated by a patient during inspiration.

The cyclic peptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, the cyclic peptides may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the cyclic peptide may be in a dried and particulate form. In a preferred embodiment, the particles are between about 0.5 and 6.0 μm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 μm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

In one preferred embodiment, a dry powder inhaler is employed which includes a piezoelectric crystal that deaggregates a dry powder dose, creating a small powder "cloud." Once the powder cloud is generated, an electrico-statically charged plated above the powder cloud lifts the drug into the air stream. The user with one relatively easy breath can then inhale the powder. The device may be breath activated, utilizing a flow sensor that activates the electronic components upon the start of inhalation, and thereby eliminating the need for coordination of activation and breathing rhythms by the user.

Routes of Administration. If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount. In general, the actual quantity of cyclic peptide of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of this invention that is sufficient to therapeutically alleviate sexual dysfunction in a patient, or to prevent or delay onset or recurrence of the sexual dysfunction.

In general, the cyclic peptides of this invention are highly active, with dose responses as low as 0.1 μg/kg, and optimal or peak dose responses between about 0.1 μg/kg and 25 μg/kg, depending on the specific peptide and the route of administration. For example, the cyclic peptide can be administered at 0.01, 0.05, 0.1, 0.5, 1, 5, 10, 50, 100, or 500 μg/kg body weight, depending on specific peptide selected, the desired therapeutic response, the route of administration, the formulation and other factors known to those of skill in the art.

The cyclic peptides of this invention typically show a "bell-shaped" dose response. That is, at increasing doses the desired biological or physiological response increases, reaches a peak or optimal response, and may thereafter decrease with further increasing doses. Conventional dose response studies and other pharmacological means may be employed to determine the optimal dose for a desired effect, such as inducing penile erections, with a given peptide, given formulation and given route of administration.

Method of Use. The invention accordingly encompasses a method of treating sexual dysfunction, including erectile dysfunction and female sexual dysfunction, by administration of a therapeutically effective amount of any of the cyclic peptides of the invention, including without limitation the cyclic peptides of any of formula I to XI.

Combination Therapy

It is also possible and contemplated to use C-terminus free acid cyclic peptides of this invention in combination with other drugs or agents. These other drugs and agents may include agents that induce erectile activity, including phosphodiesterase-5 (PDE-5) inhibitors, testosterone, prostaglandin and the like. In a preferred embodiment of the invention, cyclic peptides of the invention are used in combination with a therapeutically effective amount of a cyclic-GMP-specific phosphodiesterase inhibitor or an alpha-adrenergic receptor antagonist. Similarly, the cyclic peptides of this invention may be used in combination with any known mechanical aids or devices.

The present invention thus provides methods of treating sexual dysfunction, the methods comprising the step of administering to the patient having or at risk of having sexual dysfunction a therapeutically effective amount of a cyclic peptide of this invention in combination with a therapeutically effective amount of a second sexual dysfunction pharmaceutical agent. The cyclic peptide of this invention may be administered simultaneously with, prior to or subsequent to administration with a therapeutically effective amount of a second sexual dysfunction pharmaceutical agent. Preferably the peptide of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the peptide of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the peptide of this invention when desired or needed by the patient.

The present invention thus provides methods of treating sexual dysfunction, the methods comprising the step of administering to a patient having or at risk of having sexual dysfunction a therapeutically effective amount of a cyclic peptide of this invention in combination with another compound that is useful in the treatment of sexual dysfunction.

In a preferred embodiment of combination therapy the sexual dysfunction is female sexual dysfunction.

In an especially preferred embodiment of combination therapy the sexual dysfunction is erectile dysfunction.

The present invention also provides pharmaceutical compositions that comprise 1) a cyclic peptide of this invention and 2) a second compound useful for the treatment of sexual dysfunction.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; androgens; selective androgen receptor modulators (SARMs); buproprion; vasoactive intestinal peptide (VIP); neutral endopeptidase inhibitors (NEP); and neuropeptide Y receptor antagonists (NPY).

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napth-thalene -2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy -2-(4-hydroxy-phenyl -benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a cyclic peptide of this invention may be used in combination with any known mechanical aids or devices.

The present invention also provides kits for the treatment of sexual dysfunction (including erectile dysfunction), the kits comprising: a first pharmaceutical composition including a cyclic peptide of this invention; a second pharmaceutical composition comprising a second compound useful for the treatment of sexual dysfunction; and, a container for the first and second compositions.

The invention is further illustrated by the following non-limiting examples.

EXAMPLE 1

Synthesis of Cyclic Peptides

The cyclic peptides were synthesized by standard solid phase peptide synthesis methods. For peptides with a C-terminus Lys, an Fmoc-Lys(Mtt)-p-alkoxybenzyl alcohol resin was transferred to a solid phase peptide synthesizer reactor with a mechanical stirrer. The Fmoc group, was removed and the next Fmoc-protected amino acid, such as for example Fmoc-Trp(Boc)-OH where the amino acid is Trp, was added to the resin through standard coupling procedures. The Fmoc protective group was removed and the remaining amino acids added individually in the correct sequence, by repeating coupling and deprotection procedures until the amino acid sequence was completed. For an Ac-Nle N-termius group, after completion of coupling with the last Fmoc-amino acid derivative, Fmoc-Nle-OH, and cleavage of the Fmoc protective group, the exposed terminal amino group was acetylated with acetic anhydride and pyridine in N,N-dimethylformamide (DMF). Orthogonally protected side chains are then removed by cleavage. For example a peptide resin with either an orthogonally protected side chain of Asp as 2-phenylisoproply (OPip) ester or Lys as 4-methyltrityl (Mtt), or both, are cleaved by treatment with 1% TFA in dicholoromethane. The deprotected peptide resin was suspended in a suitable solvent, such as DMF, dichloromethane (DCM) or 1-methyl-2-pyrrolidone (NMP), a suitable cyclic coupling reagent, such as 2-(1H-benzotriazol-1-yl)-1, 1,3,3-tetramethyluronium tetrafluoroborate (TBTU), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TBTU) or N,N'-dicyclohexylcarbodiimide/1-hydroxybenzotriazole (DCCl/HOBt) was added, and coupling initiated by use of a suitable base, such as N,N-diisopropylethylamine (DI PEA), sym-collidine or N-methylmorpholine (N MM). After cyclization, the peptide-resin was washed and the peptide cleaved from the resin and any remaining protective groups using trifluoroacetic acid (TFA) in the presence of water and 1,2-ethanedithiol (EDT). The final product was precipitated by adding cold ether and collected by filtration. Final purification was by reversed phase HPLC using a $C_{18}$ column. The purified peptide was converted to acetate salt by passage through an ion-exchange column.

EXAMPLE 2

Synthesis of Ac-Nle-cyclo(-Asp-D-His-D-Phe-Arg-Trp-Lys)-OH

The peptide Ac-Nle-cyclo(-Asp-D-His-D-Phe-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1139, and was obtained in a trifluoroacetate salt form.

EXAMPLE 3

Synthesis of Ac-Nle-cyclo(-Asp-His-Phe-Arg-Trp-Lys)-OH (SEQ ID NO:2)

The peptide Ac-Nle-cyclo(-Asp-His-Phe-Arg-Trp-Lys)-OH (SEQ ID NO:2) was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1139, and was obtained in a trifluoroacetate salt form.

EXAMPLE 4

Synthesis of Ac-Nle-cyclo(-Asp-Phe-D-Phe-Arg-Trp-Lys)-OH

The peptide Ac-Nle-cyclo(-Asp-Phe-D-Phe-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1149, and was obtained in a trifluoroacetate salt form.

EXAMPLE 5

Synthesis of Ac-Nle-cyclo(-Asp-His-D-Phe-Lys-Trp-Lys)-OH

The peptide Ac-Nle-cyclo(-Asp-His-D-Phe-Lys-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1111, and was obtained in a trifluoroacetate salt form.

EXAMPLE 6

Synthesis of Ac-Nle-cyclo(-Asp-Trp-D-Phe-Arg-Trp-Lys)-OH

The peptide Ac-Nle-cyclo(-Asp-Trp-D-Phe-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1188, and was obtained in a trifluoroacetate salt form.

EXAMPLE 7

Synthesis of Ac-Nle-cyclo(-Asp-His-D-Phe-D-Arg-Trp-Lys)-OH

The peptide Ac-Nle-cyclo(-Asp-His-D-Phe-D-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1139, and was obtained in a trifluoroacetate salt form.

EXAMPLE 8

Synthesis of Ac-Nle-cyclo(-Asp-His-D-Phe-Arg-D-Trp-Lys)-OH

The peptide Ac-Nle-cyclo(-Asp-His-D-Phe-Arg-D-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1139, and was obtained in a trifluoroacetate salt form.

EXAMPLE 9

Synthesis of Ahx-cyclo(-Asp-His-D-Phe-Arg-Trp-Lys)-OH

The peptide Ahx-cyclo(-Asp-His-D-Phe-Arg-Trp-Lys)-OH was synthesized by standard solid phase peptide synthesis methods. Using appropriate Fmoc protected amino acids, the method described in Example 1 was used to synthesize the peptide, except that a Boc-protected-Ahx derivative was used. This group was removed during final cleavage of the cyclized peptide from the resin. Final purification was by RP-HPLC using a $C_{18}$ column.

The peptide is a cyclic heptapeptide melanocortin peptide analog with a free acid at the C-terminus and an $NH_2$ group at the N-terminus. The cyclic peptide has a net molecular weight of 1211, and was obtained in a trifluoroacetate salt form.

EXAMPLE 10

Synthesis of Ac-Nle-cyclo(-Asp-Tyr-D-Phe-Arg-Trp-Lys)-OH

The peptide Ac-Nle-cyclo(-Asp-Tyr-D-Phe-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1165, and was obtained in a trifluoroacetate salt form.

EXAMPLE 11

Synthesis of Ac-Nle-cyclo(-Asp-His-D-Phe(4-Cl)-Arg-Trp-Lys)-OH

The peptide Ac-Nle-cyclo(-Asp-His-D-Phe(4-Cl)-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1174, and was obtained in a trifluoroacetate salt form.

EXAMPLE 12

Synthesis of Ac-Nle-cyclo(-Asp-His-D-Ph-Orn-Trp-Lys)-OH

The peptide Ac-Nle-cyclo(-Asp-His-D-Phe-Orn-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1097, and was obtained in a trifluoroacetate salt form.

EXAMPLE 13

Synthesis of Nle-cyclo(-Asp-His-D-Phe-Arg-Trp-Lys)-OH

The peptide Nle-cyclo(-Asp-His-D-Phe-Arg-Trp-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an amino group at the N-terminus. The cyclic peptide has a net molecular weight of 1211, and was obtained in a trifluoroacetate salt form.

EXAMPLE 14

Synthesis of Ac-Nle-cyclo(-Asp-His-D-Phe-Arg-Nal 1-Lys)-OH

The peptide Ac-Nle-cyclo(-Asp-His-D-Phe-Arg-Nal 1-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1150, and was obtained in a trifluoroacetate salt form.

EXAMPLE 15

Synthesis of Ac-Nle-cyclo(-Asp-His-D-Phe-Arg-Bip-Lys)-OH

The peptide Ac-Nle-cyclo(-Asp-His-D-Phe-Arg-Bip-Lys)-OH was synthesized by standard solid phase peptide synthesis methods. Using appropriate Fmoc protected amino acids, the method described in Example 1 was used to synthesize the peptide. Final purification was by RP-HPLC using a $C_{18}$ column.

The peptide is a cyclic heptapeptide melanocortin peptide analog with a free acid at the C-terminus and an acylated amino group at the N-terminus. The cyclic peptide has a net molecular weight of 1176, and was obtained in a trifluoroacetate salt form.

Utilizing the assay procedure, the relative binding percentages and functional status were determined as shown on Table 1.

In a separate experiment, binding of Ac-Nle-cyclo(-Asp-His-D-Phe-Lys-Trp-Lys)-OH to each of MC1-R, MC3-R, MC4-R and MC5-R was titrated, and $K_i$ values determined. For Ac-Nle-cyclo( -Asp-His-D-Phe-Lys-Trp-Lsy)-OH, the $K_i$ value for MC1-R was 9.9 nM, for MC3-R was 10,800 nM, for MC4-R was 742 μM and for MC5-R was 2,530 nM.

TABLE 1

| Cyclic Peptide | Percent Inhibition At 1 μM concentration | | | | Functional Activity at |
|---|---|---|---|---|---|
| | MC1-R | MC3-R | MC4-R | MC5-R | MC4-R |
| Ac-Nle-cyclo(-Asp-D-His-D-Phe-Arg-Trp-Lys)-OH | 41 | 11 | 9 | 8 | Inactive |
| Ac-Nle-cyclo(-Asp-His-Phe-Arg-Trp-Lys)-OH (SEQ ID NO:2) | 21 | 11 | 4 | 7 | Inactive |
| Ac-Nle-cyclo(-Asp-Phe-D-Phe-Arg-Trp-Lys)-OH | 93 | 37 | 88 | 54 | Agonist |
| Ac-Nle-cyclo(-Asp-His-D-Phe-Lys-Trp-Lys)-OH | 86 | 8 | 46 | 17 | Agonist |
| Ac-Nle-cyclo(-Asp-Trp-D-Phe-Arg-Trp-Lys)-OH | 73 | 42 | 82 | 70 | Agonist |
| Ac-Nle-cyclo(-Asp-His-D-Phe-D-Arg-Trp-Lys)-OH | 0 | 10 | 4 | 13 | Inactive |
| Ac-Nle-cyclo(-Asp-His-D-Phe-Arg-D-Trp-Lys)-OH | 96 | 33 | 77 | 49 | Agonist |
| Ahx-cyclo(-Asp-His-D-Phe-Arg-Trp-Lys)-OH | 80 | 28 | 72 | 39 | Agonist |
| Ac-Nle-cyclo(-Asp-Tyr-D-Phe-Arg-Trp-Lys)-OH | 87 | 48 | 87 | 63 | Agonist |
| Ac-Nle-cyclo(-Asp-His-D-Phe(4-Cl)-Arg-Trp-Lys)-OH | 99 | 93 | 99 | 98 | Agonist |
| Ac-Nle-cyclo(-Asp-His-D-Phe-Orn-Trp-Lys)-OH | 47 | 6 | 21 | 12 | Inactive |
| Nle-cyclo(-Asp-His-D-Phe-Arg-Trp-Lys)-OH | 94 | 59 | 96 | 68 | Agonist |
| Ac-Nle-cyclo(-Asp-His-D-Phe-Arg-Nal 1-Lys)-OH | 89 | 22 | 81 | 22 | Agonist |
| Ac-Nle-cyclo(-Asp-His-D-Phe-Arg-Bip-Lys)-OH | 62 | 0 | 12 | 18 | Inactive |
| cyclo(-Succ-His-D-Phe-Arg-Trp-Lys)-OH | 56 | 0 | 29 | 0 | Agonist |

EXAMPLE 16

Synthesis of Cyclo(-Succ-His-D-Phe-Arg-Trp-Lys)-OH

The peptide cyclo(-Succ-His-D-Phe-Arg-Trp-Lys)-OH was synthesized by standard solid phase peptide synthesis methods. Using appropriate Fmoc protected amino acids, the method described in Example 1 was used to synthesize the peptide except that succinic anhydride was used to introduce a succinyl residue (Succ) at the N-terminus. Final purification was by RP-HPLC using a $C_{18}$ column.

The peptide is a cyclic des amino-hexapeptide melanocortin peptide analog with a free acid at the C-terminus. The cyclic peptide has a net molecular weight of 969, and was obtained in a trifluoroacetate salt form.

EXAMPLE 17

Comparative Binding of Cyclic Peptides to Melanocortin Receptors

Relative binding was determined by competitive inhibition using α-MSH. B16-F1 mouse melanoma cells were used as the source of MC1 receptors; HEK 293 cells, transfected with human melanocortin receptor sequences, were used as the source of MC3, MC4 and MC5 receptors. A standard competitive binding assay protocol as described above was following, using $^{125}$I-NDP-MSH as the radioligand.

Separately, stimulation of intracellular cAMP production by each of the cyclic peptides of Examples 2 to 16 was determined utilizing transfected HEK-293 cells expressing hMC4-R. A standard cAMP stimulation and measurement protocol as described above was followed.

EXAMPLE 18

Induction of Penile Erections

The ability of selected cyclic peptides of Examples 2 to 16 to induce penile erection in male rats was evaluated. Male Sprague-Dawley rats weighing 200–250 g were kept on a 12 hour on/off light cycle with food and water ad libitum. All behavioral studies were performed between 10 a.m. and 5 p.m. Groups of 6 rats were treated with peptides at a variety of doses, primarily 3 μg/kg, via intravenous administration. Immediately after administration, rats were placed into individual polystyrene cages (27 cm long, 16 cm wide, and 25 cm high) for behavioral observation. Rats were observed for 30 minutes and the number of yawns, grooming bouts and penile erections were recorded in three 10-minute bins. Each of the reported selected cyclic peptides of Table 2 was observed to induce penile erections in male rats by intravenous injection at one or more dose levels, using saline as a control. Using the above procedure, the mean number of penile erections for each rat on intravenous administration of 3 μg/kg was determined as shown on Table 2.

TABLE 2

| Cyclic Peptide | Mean PE/Rat |
|---|---|
| Ac-Nle-cyclo-(-Asp-D-His-D-Phe-Arg-Trp-Lys)-OH | 0.33 |
| Ac-Nle-cyclo-(Asp-Phe-D-Phe-Arg-Trp-Lys)-OH | 0.33 |
| Ac-Nle-cyclo-(Asp-His-D-Phe-Lys-Trp-Lys)-OH | 1.33 |
| Ac-Nle-cyclo-(Asp-Trp-D-Phe-Arg-Trp-Lys)-OH | 0.5 |
| Ac-Nle-cyclo-(Asp-His-D-Phe-Arg-D-Trp-Lys)-OH | 0.83 |
| Ahx-cyclo-(Asp-His-D-Phe-Arg-Trp-Lys)-OH | 0.33 |
| Ac-Nle-cyclo-(Asp-Tyr-D-Phe-Arg-Trp-Lys)-OH | 0.67 |

TABLE 2-continued

| Cyclic Peptide | Mean PE/Rat |
| --- | --- |
| Ac-Nle-cyclo-(Asp-His-D-Phe(4-Cl)-Arg-Trp-Lys)-OH | 0.33 |
| Ac-Nle-cyclo-(Asp-His-D-Phe-Arg-Nal 1-Lys)-OH | 0.33 |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

The invention claimed is:

1. A method for stimulating sexual response in a mammal, comprising administering a pharmaceutically sufficient amount of a composition comprising a cyclic peptide selected from the group consisting of:

Ac-Nle-cyclo(-Asp-D-His-D-Phe-Arg-Trp-Lys)-OH,
Ac-Nle-cyclo(-Asp-His-Phe-Arg-Trp-Lys)-OH (SEQ ID NO:2),
Ac-Nle-cyclo(-Asp-Phe-D-Phe-Arg-Trp-Lys)-OH,
Ac-Nle-cyclo(-Asp-His-D-Phe-Lys-Trp-Lys)-OH,
Ac-Nle-cyclo(-Asp-Trp-D-Phe-Arg-Trp-Lys)-OH,
Ac-Nle-cyclo(-Asp-His-D-Phe-D-Arg-Trp-Lys)-OH,
Ac-Nle-cyclo(-Asp-His-D-Phe-Arg-D-Trp-Lys)-OH,
Ahx-cyclo(-Asp-His-D-Phe-Arg-Trp-Lys)-OH,
Ac-Nle-cyclo(-Asp-Tyr-D-Phe-Arg-Trp-Lys)-OH,
Ac-Nle-cyclo(-Asp-His-D-Phe(4-Cl)-Arg-Trp-Lys)-OH,
Ac-Nle-cyclo(-Asp-His-D-Phe-Orn-Trp-Lys)-OH,
Nle-cyclo(-Asp-His-D-Phe-Arg-Trp-Lys)-OH,
Ac-Nle-cyclo(-Asp-His-D-Phe-Arg-Nal 1-Lys)-OH,
Ac-Nle-cyclo(-Asp-His-D-Phe-Arg-Bip-Lys)-OH, and
Cyclo(-Succ-His-D-Phe-Arg-Trp-Lys)-OH, or a pharmaceutically acceptable salt thereof, for a time and under conditions effective to stimulate a sexual response.

2. The method of claim 1 wherein said composition further comprises a pharmaceutically acceptable carrier.

3. The method of claim 1 wherein administering comprises a method of administration selected from the group consisting of administration by injection, administration through mucous membranes, buccal administration, oral administration, urethral administration, vaginal administration, dermal administration, inhalation administration and nasal administration.

4. The method of claim 3, wherein administering comprises nasal administration of a metered amount of a formulation comprising an aqueous buffer.

5. The method of claim 4, wherein the aqueous buffer is a member selected from the group consisting of saline buffer and citrate buffer and a mixture thereof.

6. The method of claim 1 wherein the mammal is a male.

7. The method of claim 6 wherein the sexual response is penile erection.

8. The method of claim 1 wherein the mammal is a female.

9. The method of claim 8 wherein the sexual response is female sexual arousal.

10. A synthetic cyclic peptide wherein the peptide is:
Ac-Nle-cyclo(-Asp-D-His-D-Phe-Arg-Trp-Lys)-OH,
Ac-Nle-cyclo(-Asp-His-Phe-Arg-Trp-Lys)-OH (SEQ ID NO:2),
Ac-Nle-cyclo(-Asp-Phe-D-Phe-Arg-Trp-Lys)-OH,
Ac-Nle-cyclo(-Asp-His-D-Phe-Lys-Trp-Lys)-OH,
Ac-Nle-cyclo(-Asp-Trp-D-Phe-Arg-Trp-Lys)-OH,
Ac-Nle-cyclo(-Asp-His-D-Phe-D-Arg-Trp-Lys)-OH,
Ac-Nle-cyclo(-Asp-His-D-Phe-Arg-D-Trp-Lys)-OH,
Ahx-cyclo(-Asp-His-D-Phe-Arg-Trp-Lys)-OH,
Ac-Nle-cyclo(-Asp-Tyr-D-Phe-Arg-Trp-Lys)-OH,
Ac-Nle-cyclo(-Asp-His-D-Phe(4-C1)-Arg-Trp-Lys)-OH,
Ac-Nle-cyclo(-Asp-His-D-Phe-Orn-Trp-Lys)-OH,
Nle-cyclo(-Asp-His-D-Phe-Arg-Trp-Lys)-OH,
Ac-Nle-cyclo(-Asp-His-D-Phe-Arg-Nal 1-Lys)-OH,
Ac-Nle-cyclo(-Asp-His-D-Phe-Arg-Bip-Lys)-OH, and
Cyclo(-Succ-His-D-Phe-Arg-Trp-Lys)-OH.

11. A pharmaceutical composition comprising a cyclic peptide of claim 10 or a pharmaceutical salt thereof and a pharmaceutically accentable carrier.

12. The pharmaceutical composition of claim 11 wherein the peptide is a MC3-R agonist.

13. The pharmaceutical composition of claim 11 wherein the peptide is a MC4-R agonist.

14. The pharmaceutical composition of claim 11 wherein the peptide is in a therapeutically effective amount to treat sexual dysfunction in a mammal.

15. The pharmaceutical composition of claim 14 wherein the mammal is a male.

16. The pharmaceutical composition of claim 14 wherein the sexual dysfunction is erectile dysfunction.

17. The pharmaceutical composition of claim 14 wherein the mammal is a female.

18. The pharmaceutical composition of claim 14 wherein the dysfunction is female sexual dysfunction.

19. A synthetic peptide consisting of Ac-Nle-cyclo(-Asp-His-D-Phe-Lys-Trp-Lys)-OH.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: alpha-melanocyte stimulating hormone
      tetrapeptide core sequence

<400> SEQUENCE: 1

His Phe Arg Trp
1

<210> SEQ ID NO 2
<211> LENGTH: 7
<212> TYPE: PRT
<213> ORGANISM: Artificial
<220> FEATURE:
<223> OTHER INFORMATION: Synthetic cyclic free acid peptide for
      treatment of sexual dysfunction
<220> FEATURE:
<221> NAME/KEY: MISC_FEATURE
<222> LOCATION: (1)..(1)
<223> OTHER INFORMATION: where Xaa is norleucine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(7)
<223> OTHER INFORMATION: Cyclicized through amind bond between side
      chains of Asp and Lys

<400> SEQUENCE: 2

Xaa Asp His Phe Arg Trp Lys
1               5
```